US010842634B2

(12) United States Patent
Pasini et al.

(10) Patent No.: US 10,842,634 B2
(45) Date of Patent: Nov. 24, 2020

(54) STRUCTURAL POROUS BIOMATERIAL AND IMPLANT FORMED OF SAME

(71) Applicant: THE ROYAL INSTITUTION FOR THE ADVANCEMENT OF LEARNING/MCGILL UNIVERSITY, Montreal (CA)

(72) Inventors: Damiano Pasini, Montreal (CA); Michael Tanzer, Hampstead (CA); Sajad Khanoki Arabnejad, Montreal (CA); Burnett Johnston, Calgary (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 428 days.

(21) Appl. No.: 15/308,485

(22) PCT Filed: May 4, 2015

(86) PCT No.: PCT/CA2015/050384
§ 371 (c)(1),
(2) Date: Nov. 2, 2016

(87) PCT Pub. No.: WO2015/164982
PCT Pub. Date: Nov. 5, 2015

(65) Prior Publication Data
US 2017/0095337 A1  Apr. 6, 2017

Related U.S. Application Data

(60) Provisional application No. 61/987,950, filed on May 2, 2014.

(51) Int. Cl.
*A61F 2/30* (2006.01)
*A61L 27/56* (2006.01)
(Continued)

(52) U.S. Cl.
CPC ........... *A61F 2/30767* (2013.01); *A61F 2/36* (2013.01); *A61F 2/3662* (2013.01);
(Continued)

(58) Field of Classification Search
CPC .......... A61F 2/30767; A61F 2002/3092; A61F 2002/30275; A61F 2002/3028; A61F 2002/30273; A61L 27/56; A61L 27/50
See application file for complete search history.

(56) References Cited

U.S. PATENT DOCUMENTS 5,458,641 A * 10/1995 Ramirez Jimenez ..... A61F 2/44
403/43
6,069,295 A * 5/2000 Leitao ................ A61F 2/30767
433/201.1
(Continued)

FOREIGN PATENT DOCUMENTS

CA    2860013    6/2013
CA    2947775    11/2015
(Continued)

OTHER PUBLICATIONS

International Search Report, PCT/CA2015/050384, dated Jul. 22, 2015.
(Continued)

*Primary Examiner* — Brian A Dukert
(74) *Attorney, Agent, or Firm* — Norton Rose Fulbright Canada

(57) ABSTRACT

An implant comprising a porous microstructure is disclosed which has an external surface, where at least a region of the external surface is formed of the porous microstructure. The microstructure is defined by at least one lattice of cells. Each cell has a predetermined cell topology and a plurality of edges. One or more of the edges of each cell connect to an adjacent cell along a corresponding edge thereof. Collec-
(Continued)

tively, the cells have a periodic or aperiodic arrangement within the at least one lattice.

26 Claims, 14 Drawing Sheets

(51) Int. Cl.
*A61F 2/36* (2006.01)
*A61L 27/36* (2006.01)

(52) U.S. Cl.
CPC .............. *A61L 27/365* (2013.01); *A61L 27/56* (2013.01); *A61F 2/367* (2013.01); *A61F 2/3672* (2013.01); *A61F 2/3676* (2013.01); *A61F 2002/3028* (2013.01); *A61F 2002/3092* (2013.01); *A61F 2002/30275* (2013.01); *A61L 2430/02* (2013.01)

(56) References Cited

U.S. PATENT DOCUMENTS

| | | | |
|---|---|---|---|
| 6,993,406 | B1 | 1/2006 | Cesarano et al. |
| 7,537,664 | B2 | 5/2009 | O'Neill et al. |
| 7,718,109 | B2 | 5/2010 | Robb et al. |
| 8,147,861 | B2 | 4/2012 | Jones et al. |
| 8,268,099 | B2 | 9/2012 | O'Neill et al. |
| 8,268,100 | B2 | 9/2012 | O'Neill et al. |
| 8,350,186 | B2 | 1/2013 | O'Neill et al. |
| 8,728,387 | B2 | 5/2014 | Jones et al. |
| 8,992,703 | B2 | 3/2015 | O'Neill et al. |
| 9,135,374 | B2 | 9/2015 | Jones et al. |
| 9,180,010 | B2* | 11/2015 | Dong ................. A61F 2/28 |
| 9,456,901 | B2 | 10/2016 | Jones et al. |
| 2003/0236573 | A1* | 12/2003 | Evans ................. A61L 27/12 623/23.58 |
| 2006/0147332 | A1* | 7/2006 | Jones ................. A61F 2/2803 419/8 |
| 2006/0276925 | A1 | 12/2006 | Lin et al. |
| 2007/0203584 | A1* | 8/2007 | Bandyopadhyay ...... A61F 2/28 623/23.5 |
| 2010/0298950 | A1* | 11/2010 | McDonnell ......... A61F 2/30771 623/23.53 |
| 2011/0014081 | A1* | 1/2011 | Jones .................. A61F 2/2803 419/2 |
| 2011/0202140 | A1 | 8/2011 | Turner et al. |
| 2013/0218288 | A1 | 8/2013 | Fonte et al. |
| 2014/0363481 | A1 | 12/2014 | Pasini et al. |
| 2017/0095337 | A1 | 4/2017 | Pasini et al. |

FOREIGN PATENT DOCUMENTS

| | | | |
|---|---|---|---|
| EP | 2606859 | | 6/2013 |
| EP | 2793756 | | 10/2014 |
| EP | 3137125 | | 1/2018 |
| WO | 9933641 | * | 7/1999 |
| WO | 2005051233 | | 11/2006 |
| WO | 2008146141 | | 12/2008 |
| WO | 2013091085 | | 6/2013 |
| WO | 2013181375 | | 12/2013 |
| WO | 2015164982 | | 11/2015 |

OTHER PUBLICATIONS

Banhart, "Manufacture, characterisation and application of cellular metals and metal foams", Progress in Material Science 46 (2001) 559-632, 2001.

Extended European Search Report, EP 15785261.7, dated Dec. 6, 2017.

Lin, D., Qing, L., W., Zhou, S., and Swain, M.V. Design Optimization of Functionally Graded Dental Implant for Bone Remodelling. Composites: Part B 40 (2009) 668-675. Available online Apr. 21, 2009 (Apr. 21, 2009). Retrieved from the Internat [Retrieved Apr. 2, 2013].

Tang, C.Y., Guo, Y.Q., Tsui, C.P., and Gao, B. Multi-scale Finite Element Analysis on Biomechanical Response of Functionally Graded Dental implant/Mandible System. Journal of the Serbian Society of Computational Mechanics: vol. 1 No. 1 (2007) 164-173. Retrieved from the Internat [Retrieved Apr. 2, 2013].

Rungsiyakull, C., Li, Q., Sun, G., Li, W., and Swain, M.V. Surface Morphology Optimization for Osseointegration of Coated Implants. Biomaterials 31 (2010) 7196-7204. Available online Jun. 22, 2010 (Jun. 22, 2010). Retrieved from the Internet [Retrieved Apr. 2, 2013].

Extended European Search Report, EP 12859682.2, dated Jul. 28, 2015.

* cited by examiner

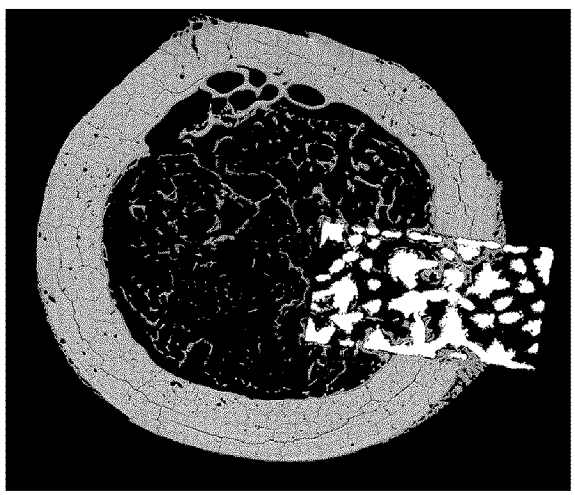
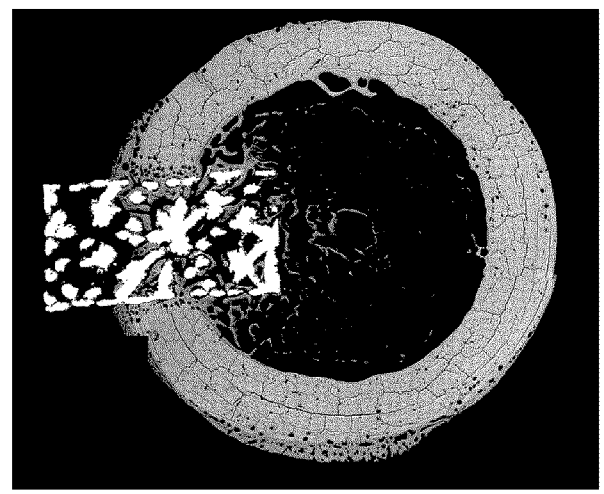
FIG. 5A
FIG. 5B
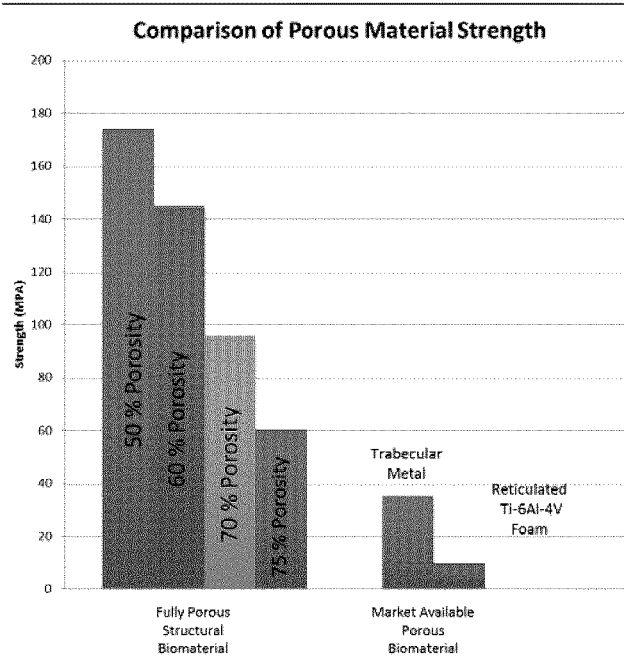
FIG. 5C

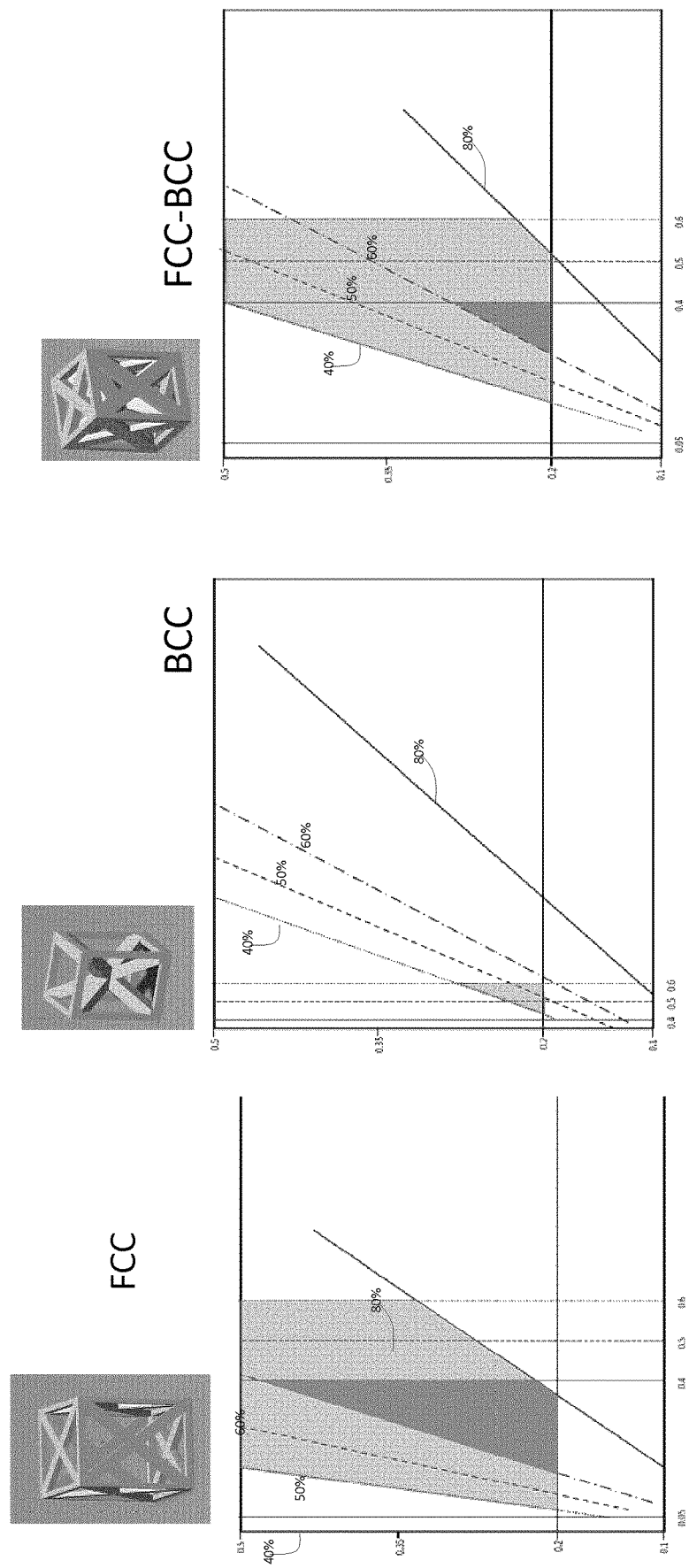

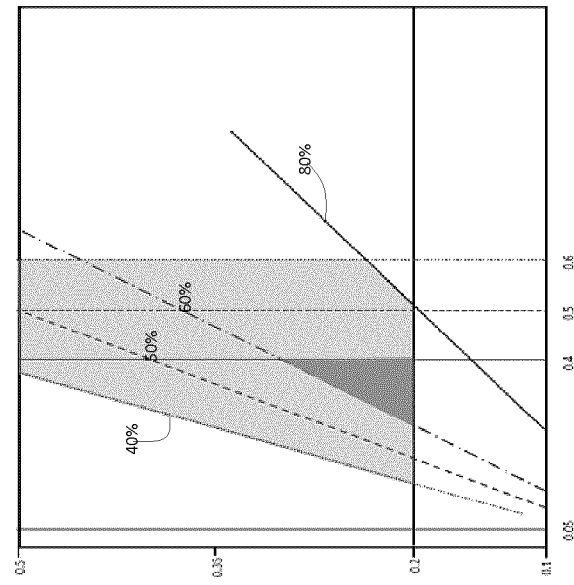
Fig. 16
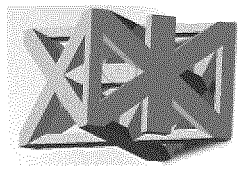
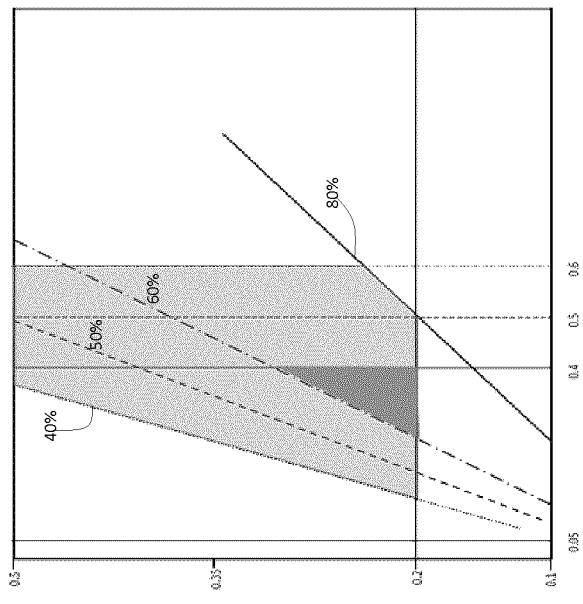
Fig. 15
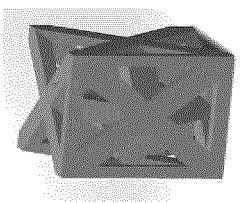

STRUCTURAL POROUS BIOMATERIAL AND IMPLANT FORMED OF SAME

TECHNICAL FIELD

The application relates generally to prosthetic implants, and, more particularly, to an implant with a porous microstructure for bone replacement.

BACKGROUND

Certain existing orthopedic and dental bone-replacement implants are formed of a material, or are surface treated with an external coating or material, which is intended to encourage bone ingrowth from the local bone tissue against or within which they are implanted. For example, implants used in total hip replacement formed of a microstructural material over a fully dense material have been attempted. Hip implants with porous tantalum have also been proposed in knee and hip replacement surgery. (Bobyn et al., 2004, The Journal of Bone and Joint Surgery, 86: 123).

Open cell structures for bone implants formed of tantalum applied by chemical vapor deposition onto a carbon foam substrate are also known, as described for example in U.S. Pat. No. 5,282,861 by Kaplan, which provides bone implants so formed which are intended to mimic the microstructure of cancellous bone. Such tantalum foam is an excellent material due to its biocompatibility, high volumetric porosity, and modulus of elasticity similar to that of bone. To create this tantalum foam, pure tantalum is chemically deposited on a carbon foam skeleton. Consequently, the microstructure of a tantalum foam implant has an almost uniform and random distribution of pore shape and size throughout the implant.

These material characteristics, however, have been found to be less capable of solving the conflicting nature of the physiological phenomena occurring in an implant (Kuiper and Huiskes, 1992, Recent Advances in Computer Methods in Biomechanics & Biomedical Engineering, J. Middleton, G N Pande and K R Williams, 76-84; Kuiper and Huiskes, 1997, Transactions-American Society of Mechanical Engineers Journal of Biomechanical Engineering, 1919: 166-174). Whereas the reduced stiffness of the foam decreases bone resorption, the uniform distribution of cells has the undesired effect of increasing the interface stresses.

Accordingly, while these known implants and porous biomaterials permit bone ingrowth, they may not always provide the strength required for all applications, particularly those where load-bearing bone replacement is required. Additionally, the properties of these biomaterials, and thus the bone implants formed thereby, cannot typically be modified or selected based on the requirements of the given application and/or patient, and are thus difficult to design for the specific local bone tissue of a patient.

Bone-replacement implants formed of graded cellular materials having a non-homogenous distribution of material properties therefore continue to be developed, in an attempt to address at least some of the above-noted challenges associated with known implants and porous biomaterials.

SUMMARY OF THE INVENTION

In accordance with one aspect of the present invention, there is provided an implant one or more surfaces of which are adapted to be disposed against bone tissue, the implant comprising: an external surface at least a portion of which is comprised of a porous microstructure and adapted to abut the bone tissue, the porous microstructure formed by an additive-manufactured lattice of a plurality of cells, the lattice and the cells being designed and pre-selected prior to manufacturing such as to have predetermined structural characteristics; wherein the cells of the lattice have at least one predetermined cell topology and each of the cells is formed by a plurality of struts defining pores of the cell therebetween, at least one strut of each cell connecting to a strut of an adjacent one of the cells within the lattice along a corresponding edge thereof, the struts having a strut thickness of between 70 µm and 400 µm the pores of the cell having a mean pore size of between 50 µm and 800 µm, the predetermined cell topology being selected from a group consisting of: octet truss; tetrahedron; octahedron; Body-Centered Cube (BCC); Face-Centered Cube (FCC); rhombicuboctahedron; rhombic dodecahedron; and any combination of one or more of these cell topologies and modified versions thereof; wherein the lattice defines a predetermined and designed tessellation and arrangement of said cells forming the lattice, cell the lattice having a porosity of greater than 30%; and wherein the porous microstructure has a mechanical strength substantially similar to that of the bone tissue against which said one or more surfaces of the implant are disposed.

In accordance with another aspect of the present invention, there is provided a method for manufacturing the implant as described above, comprising depositing layers of a biocompatible material on a non-foam substrate according to a pre-determined sequence of layering, thereby forming said porous microstructure.

In accordance with another aspect of the present invention, there is provided a method for manufacturing an implant comprising: pre-selecting a designed porous microstructure having a lattice composed of cells, including selecting a one or more predetermined cell topologies, selecting a predetermined porosity, cell strut thickness and packing factor of the lattice, and selecting an arrangement of the cells within the lattice to have a periodic or aperiodic arrangement; and using additive manufacturing to form the implant, including repeatedly depositing layers of a biocompatible material to form said designed lattice of cells, and forming the designed porous microstructure in at least a region of at least an external surface of the implant adapted to be disposed proximate bone tissue, the designed porous lattice microstructure having said one or more predetermined cell topologies and said predetermined porosity, cell strut thickness and packing factor.

In accordance with another aspect of the present invention, there is also provided a structural porous biomaterial comprising a designed microtruss having a porous lattice microstructure composed of cells, a majority of the cells being open and having tissue reception surfaces permitting bone ingrowth therein, said cells having a predetermined cell topology selected from the group consisting of: octet truss; tetrahedron; octahedron; Body-Centered Cube (BCC); Face-Centered Cube (FCC); rhombicuboctahedron; rhombic dodecahedron; and any combination of one or more of these cell topologies and modified versions thereof; and wherein the cells of the porous lattice microstructure are arranged to form an interconnected network of said cells, the porous lattice microstructure having a porosity of greater than 30%, and the cells have a mean pore size of between 50 µm and 800 µm and a cell strut thickness of each unit cell of between 70 µm and 400 µm.

In accordance with a further aspect of the present invention, there is provided the implant and/or structural porous biomaterial as described above, wherein said tessellation and said arrangement of the cells are uniform throughout the lattice.

In accordance with a further aspect of the present invention, there is provided the implant and/or structural porous biomaterial as described above, wherein the arrangement of the cells within the lattice is fully periodic or fully aperiodic.

In accordance with a further aspect of the present invention, there is provided the implant and/or structural porous biomaterial as described above, wherein the arrangement of the cells within the lattice is a combination of periodic and aperiodic.

In accordance with a further aspect of the present invention, there is provided the implant and/or structural porous biomaterial as described above, wherein the cells are fully tessellated and a packing factor of the cells connected to one another within the lattice is about 100%.

In accordance with a further aspect of the present invention, there is provided the implant and/or structural porous biomaterial as described above, wherein gaps are defined between adjacent and interconnected cells within the lattice, a packing factor of the cells being less than 100%.

In accordance with a further aspect of the present invention, there is provided the implant and/or structural porous biomaterial as described above, wherein the cell topology of the cells of the lattice is identical throughout the lattice.

In accordance with a further aspect of the present invention, there is provided the implant and/or structural porous biomaterial as described above, wherein the cells of the lattice comprise two or more different cell topologies.

In accordance with a further aspect of the present invention, there is provided the implant and/or structural porous biomaterial as described above, wherein the porous microstructure is made from a biocompatible material selected from the group consisting of: Titanium and its alloy (such as Ti6Al4V); Steel; CoCr; Tantalum; and alloys of each thereof.

In accordance with a further aspect of the present invention, there is provided the implant and/or structural porous biomaterial as described above, wherein the porosity of the lattice is between 40% and 80%.

In accordance with a further aspect of the present invention, there is provided the implant and/or structural porous biomaterial as described above, wherein the porosity is between 50% and 80%.

In accordance with a further aspect of the present invention, there is provided the implant and/or structural porous biomaterial as described above, wherein the porosity of the lattice is non-constant.

In accordance with a further aspect of the present invention, there is provided the implant and/or structural porous biomaterial as described above, wherein the mean pore size of each of said cell varies in said porous microstructure.

In accordance with a further aspect of the present invention, there is provided the implant and/or structural porous biomaterial as described above, wherein the struts have a strut thickness of 200 μm or less.

In accordance with a further aspect of the present invention, there is provided the implant and/or structural porous biomaterial as described above, wherein at least one of a cross-sectional shape and a cross-sectional area of the struts of the cells vary within said porous microstructure.

In accordance with a further aspect of the present invention, there is provided the implant and/or structural porous biomaterial as described above, wherein the cell topology of said cell includes a Face-Centered Cube (FCC) and modifications thereof, the lattice has a porosity between 30% and 80%, a strut thickness of each said cell is at least about 70 μm, and a mean pore size of each said cell is between 50 μm and 800 μm.

In accordance with a further aspect of the present invention, there is provided the implant and/or structural porous biomaterial as described above, wherein the cell topology of each said cell includes a Body-Centered Cube (BCC) and modifications thereof, the porous microstructure has a porosity between 30% and 80%, a strut thickness of each said cell is at least about 70 μm, and a mean pore size of each said cell is between 50 μm and 800 μm.

In accordance with a further aspect of the present invention, there is provided the implant and/or structural porous biomaterial as described above, wherein the cell topology of each said cell includes a composite of Face-Centered Cube (FCC) and Body-Centered Cube (BCC), the lattice has a porosity between 30% and 80%, a strut thickness of each said cell is at least about 70 μm, and a mean pore size of each said cell is a maximum of about 800 μm.

In accordance with a further aspect of the present invention, there is provided the implant and/or structural porous biomaterial as described above, wherein the cell topology of each said cell includes an octet truss and modifications thereof, the porous microstructure has a porosity between 30% and 80%, a strut thickness of each said cell is at least about 70 μm, and a mean pore size of each said cell is a maximum of about 800 μm.

In accordance with a further aspect of the present invention, there is provided the implant and/or structural porous biomaterial as described above, wherein the cell topology of each said cell includes a rhombicuboctahedron and modifications thereof, the lattice has a porosity between 30% and 80%, a strut thickness of each cell is at least about 70 μm, and a mean pore size of each said cell is a maximum of about 800 μm.

In accordance with a further aspect of the present invention, there is provided the implant and/or structural porous biomaterial as described above, wherein the cell topology of each said cell includes a rhombic dodecahedron and modifications thereof, the lattice has a porosity between 30% and 80%, a strut thickness of each said cell is at least about 70 μm, and a mean pore size of each said cell is a maximum of about 800 μm.

In accordance with a further aspect of the present invention, there is provided the implant and/or structural porous biomaterial as described above, wherein the strut thickness of said cell is about 200 μm.

In accordance with a further aspect of the present invention, there is provided the implant and/or structural porous biomaterial as described above, wherein the struts of the cells have a surface roughness thereon, the surface roughness being in the range of 10 μm to 500 μm.

In accordance with a further aspect of the present invention, there is provided the implant and/or structural porous biomaterial as described above, wherein one or more joint between said struts of the cells have local reinforcement to improve the mechanical properties of the cells formed thereby, without materially affecting the pore size.

In accordance with a further aspect of the present invention, there is provided the implant and/or structural porous biomaterial as described above, wherein the local reinforcement includes at least one of an arc, fillet, chamfer or added material.

In accordance with a further aspect of the present invention, there is provided the implant and/or structural porous biomaterial as described above, wherein the cell topology is one of a tetrahedron, an octet truss, and modified versions thereof.

In accordance with a further aspect of the present invention, there is provided the implant and/or structural porous biomaterial as described above, wherein the porous microstructure has a strength of greater than 190 MPa at 50% porosity, greater than 115 MPa at 60% porosity, greater than 100 MPa at 70% porosity and greater than 60 MPa at 75% porosity.

There is further alternatively provided the following aspects of the present invention.

An implant, with at least one external surface adapted to be disposed against bone tissue, which comprises a porous microstructure formed on at least a portion of at least the external surface of the implant, the porous microstructure defined by at least one designed additive-manufactured lattice of cells, each of the cells of the lattice having a predetermined cell topology and a plurality of struts forming edges of the cell, at least one strut of each cell connecting to a strut of an adjacent cell along a corresponding edge thereof, the cells collectively having a periodic arrangement within the lattice, wherein the microstructure has an implant strength being substantially similar to a strength of the bone tissue.

An implant, with at least one external surface adapted to be disposed against bone tissue, which comprises a porous microstructure formed on at least a portion of at least the external surface of the implant, the porous microstructure defined by at least one designed additive-manufactured lattice of cells, each of the cells of the lattice having a predetermined cell topology and a plurality of struts forming edges of the cell, at least one strut of each cell connecting to a strut of an adjacent cell along a corresponding edge thereof, the cells collectively having an aperiodic arrangement within the lattice, wherein the microstructure has an implant strength being substantially similar to a strength of the bone tissue.

A method for manufacturing an implant which comprises forming a porous microstructure along at least a region of at least an external surface of the implant, including using additive manufacturing to repeatedly deposit layers of a biocompatible material on the region to form at least one pre-designed lattice of cells, each cell of said lattice having a predetermined cell topology and a plurality of edges, at least one edge of each cell connecting to an adjacent cell along a corresponding edge thereof, the cells collectively having a predetermined periodic or aperiodic arrangement within the lattice.

A method for manufacturing an implant which comprises pre-selecting a designed porous lattice microstructure composed of cells, including selecting a one or more predetermined cell topologies and selecting a predetermined porosity, cell strut thickness and packing factor of the lattice, and using additive manufacturing to form the implant, including forming the designed porous lattice microstructure in at least a region of at least an external surface of the implant adapted to be disposed proximate to bone tissue, the designed porous lattice microstructure having said one or more predetermined cell topologies and said predetermined porosity, cell strut thickness and packing factor.

BRIEF DESCRIPTION OF THE DRAWINGS

Reference is now made to the accompanying figures in which:

FIGS. 5A and 5B depict the results of a bone ingrowth study of a sample composed of a lattice having a tetrahedron based cell topology, measured at 4 and 8 weeks respectively;

FIG. 5C is a graph depicting strength (measured in MPa and sown on the Y-axis) of the fully porous structural biomaterial as described herein in comparison with existing porous biomaterial of the prior art;

FIG. 6 is a graph showing nominal cell wall thicknesses at different cell mean pore sizes and microstructure porosities for an cell porous microstructure having a Face-Centered Cube (FCC) cell topology;

FIG. 7 is a graph showing nominal cell wall thicknesses at different cell mean pore sizes and microstructure porosities for an cell porous microstructure having a Body-Centered Cube (BCC) cell topology;

FIG. 8 is a graph showing nominal cell wall thicknesses at different cell mean pore sizes and microstructure porosities for an cell porous microstructure having an FCC-BCC Composite cell topology;

FIG. 15 is a graph showing nominal cell wall thicknesses at different cell mean pore sizes and microstructure porosities for an cell porous microstructure having yet another Octet Truss cell topology; and FIG. 16 is a graph showing nominal cell wall thicknesses at different cell mean pore sizes and microstructure porosities for an cell porous microstructure having yet another Octet Truss cell topology.

DETAILED DESCRIPTION

Figure 1A:
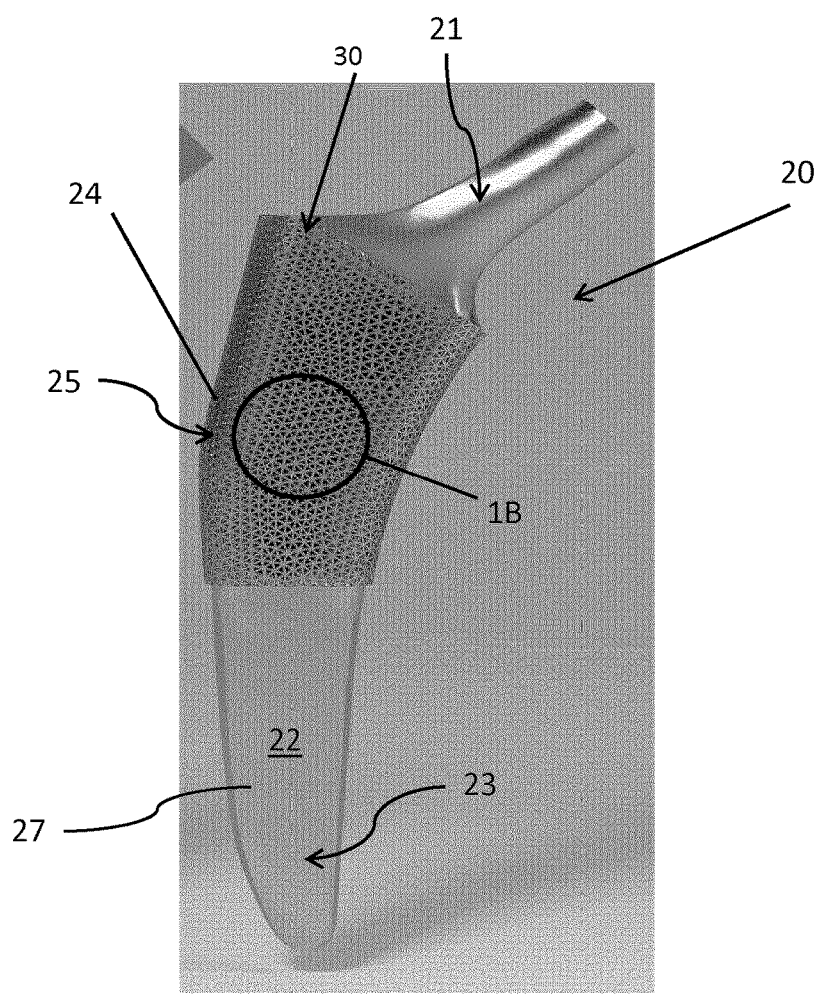
FIG. 1A is a perspective view of an implant according to an embodiment of the present disclosure, the implant having at least an external surface with a region formed of a porous cellular microstructure as described herein.

The present disclosure provides for a high-strength structural porous biomaterial, and implants formed of such a material. The implants described herein made of the present structural porous biomaterial, in contrast to most implants in current use which are made of either a fully solid or a foam material, consists of a lattice microstructure having a preselected distribution of material properties which may be specifically designed for the particular indented application and/or patient. The structural porous biomaterial described may be used for bone replacement, as an intercalary material, or forming part or all of an implant at least a surface of which is adapted to contact bone tissue, whether the implant is a bone implant, a joint replacement implant (e.g. total hip replacement, total knee replacement, etc.), as an intercalary material used to replace a vertebral disc in vertebral fusion, etc. The presently described high-strength porous biomaterial is formed by additive manufacturing processes, which enables significant opportunities for orthopedic applications. Additive manufacturing enables fully porous biomaterials which may enable significant new opportunities for orthopedic and dental implant applications. The morphological parameters of the presently described biomaterial, such as topology, porosity and pore size, can be tightly controlled to meet bone ingrowth requirements while still enabling the structure to be tailored to match the local mechanical properties of the host bone, for example with gradients of properties throughout the design.

Requirements for a successful bone tissue engineering scaffold typically include osteoconductivity, high porosity to facilitate transport of nutrients and metabolic wastes, sufficient mechanical strength to support physiological loading conditions, and appropriate biodegradability. These attributes are controlled by the pore microarchitecture, in particular by nodal connectivity, porosity, pore size as well as pore topology. Pore topology describes geometric properties independent of cell size and shape, as well as invariant to stretching, bending and twisting. The cell architecture affects functional characteristics such as elastic modulus, permeability, and diffusivity. The latter describes mass transport conditions that in turn influence cell phenotype, tissue ingrowth, and nutrient settings. Optimal trade-off cell topologies can be obtained through multi-objective topology optimization, which allows for determined cell geometry that has high vascularization and superior osteochondral ossification.

As will be seen, the biomaterial as described herein is composed of a structural microstructure 30 formed by a cell framework which is at least partially, if not fully, porous such as to facilitate and encourages bone ingrowth from the local bone tissue once implanted. More specifically, the structural microstructure 30 comprises one or more lattices 32 made up of an arrangement of individual cells 34. These cells 34 have a predetermined, and specifically designed, cell topology which defines pores of a particular size and shape. Each of these individual cells 34 is interconnected with adjacent cells in a predetermined, and specifically designed, manner, in order to form the selected lattice 32 architecture.

In all cases, the size and topology of any of the cells described herein, and the architectural structure of the resulting lattice formed thereby, are designed and predetermined prior to manufacture of the material and/or implant. In contrast to existing porous materials such as tantalum foam wherein the porosity and pore size may be substantially uniform but randomly oriented throughout the random structure of foam material, the topology, porosity and pore size of the individual cells and the resulting lattice structure of the present disclosure is not random but rather a pre-determined and thought-out architecture determined based on the requirements of the give implant, application, bone type, patient requirements, etc. which is subsequently manufactured using additive manufacturing techniques. This enables, for example gradients of properties throughout the material and/or implant, whereby certain regions of the material or implant can be for example made to be more porous or less porous, stronger or weaker, to have larger pores or smaller pores, in comparison with other regions of the material or implant. This may be desirable, for example, in order to better mimic the structure and strength of bone in terms of topology, porosity and pore size.

Referring now to FIGS. 1A to 1D, the prosthetic implant 20 generally includes an external surface 22 having a region 24 occupying some or all of the external surface 22. The region 24 of the implant 20 is adapted to be disposed against or adjacent the bone tissue against which the implant 20 is to come into contact.

The region 24 of the implant 20 at least partially includes, and optionally is entirely formed of, the structural microstructure 30 (or simply "microstructure 30"). The region 24 comprised of this microstructure 30 may extend through the full transverse thickness of the implant 20 or may alternately extend only partially therethrough such as to be formed only on outwardly-facing surfaces thereof. Regardless, the microstructure 30 is a cellular framework, comprised of a plurality of interconnected unit cells 34 which form lattices 32, which facilitates and encourages bone ingrowth from the local bone tissue once implanted. The microstructure 30 can be customized to meet the requirements of the specific anatomic location that will receive the implant 20, and it has a load-bearing capacity which reproduces the strength and strain energy density of the local bone tissue.

Irrespective of its configuration, the microstructure 30 is defined by one or more lattices 32, each having an arrangement of cells 34 whose homogenous or heterogeneous properties and relationships with one another provide the microstructure 30 with its desired functionality, which will be described in more detail below.

Figure 1B:
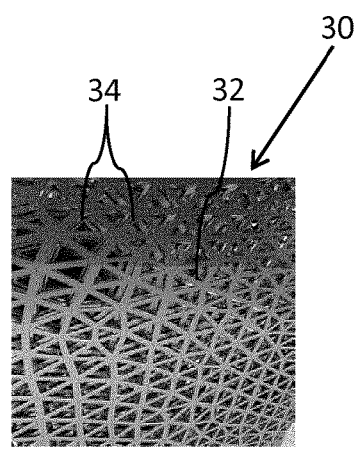
FIG. 1B is an enlarged view of a portion of the cell porous microstructure of FIG. 1A, taken from region 1B of FIG. 1A.
Figure 1C:
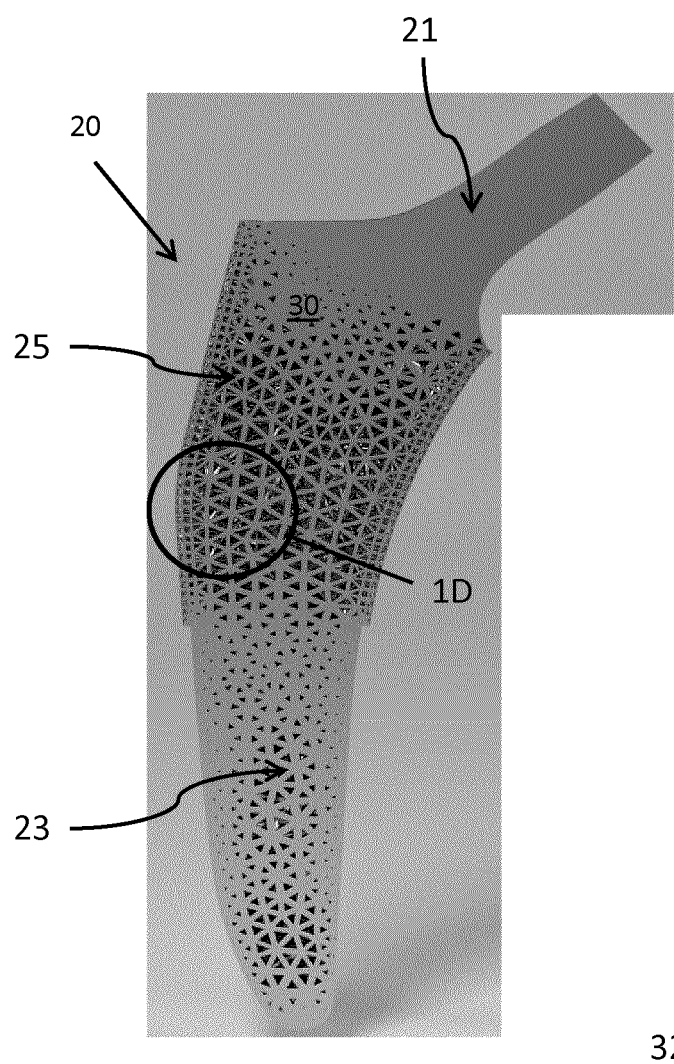
FIG. 1C is a perspective cross-sectional view of the implant of FIG. 1A.
Figure 1D:
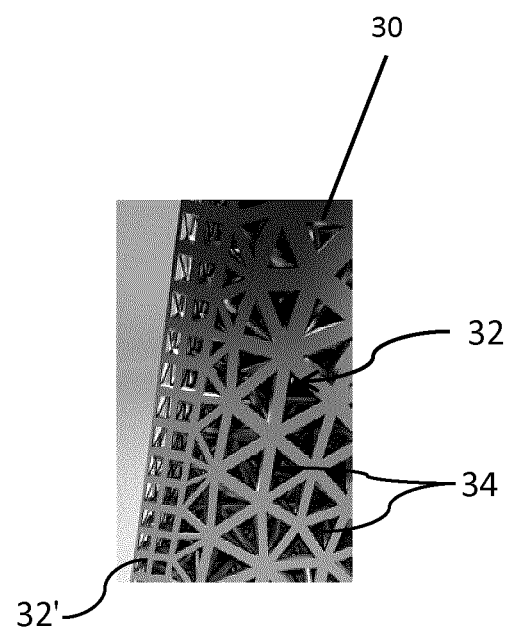
FIG. 1D is an enlarged perspective view of a portion of the implant of FIG. 1A, taken from region 1D in FIG. 1C.

As seen in both FIGS. 1B and 1D, the one or more microtruss or lattice 32 which makes up the microstructure 30 is formed by a plurality of interconnected unit cells 34. A majority of these unit cells 34 are porous, at least within regions of the implant adjacent to bone tissue such as to promote bone ingrowth therein, and the unit cells have a specific, designed and predetermined, topology. In the example of FIGS. 1B and 1D, the cells 34 have a tetrahedron topology, however other topologies are also possible, as will be seen below. The cells 34 having the selected topology (in this example, tetrahedron) are disposed together in a specific arrangement to form the lattice structure 32. The cells 34 define either a period or an aperiodic (i.e. non-periodic) arrangement of cells within the lattice 32. The difference between these two types of cell arrangements will also be described in further detail below. The cells 34 having the given topology are also fitted together within the lattice 32 with a preselected "packing factor" P, which is a measure of the "stackability" or tessellation of the cells 34 with respect to one another within their lattice 32. This accordingly influences porosity of the lattice 32. The cells 34 can therefore be designed and produced as required, for example having a designed cell topology, porosity, cell wall or strut thickness, pore size, etc.).

As best seen in the cross-sectional view of FIG. 1C, the implant 20 may include regions, such as the stem 21, which are fully solid, whereas other regions 23, 25 are formed partially or wholly of the structural porous microstructure 30. These different regions are integrally formed together and the interfaces therebetween may be gradual in order to provide a transition between the fully solid and the fully porous microstructure 30, for example. In the embodiment shown in FIGS. 1A-1B, the implant 20 includes the fully solid portion 21, for example at the stem and neck region of the femoral implant, a proximal region 25 wherein the porous microstructure 30 extends fully through the entire body of the implant and thus wherein the porous microstructure 30 is disposed on the outermost surface of the implant, and a distal portion 23 which may still be formed of the porous microstructure (as seen in FIG. 1C) but which has a solid outer surface 27 (as seen in FIG. 1A).

As seen in FIG. 1D, the lattice 32 which forms the porous microstructure 30 is formed of a plurality of the unit cells 34 having a selected topology (in this case, a tetrahedron shaped topology) and disposed together in a given arrangement. In the embodiment depicted in FIGS. 1A-1D, the tetrahedron shaped cells 34 are arranged together in an aperiodic arrangement wherein the tetrahedron cells 34 are skewed and packed together without any gaps and overlaps (i.e. a fully tessellated lattice arrangement defining a Packing Factor (P) of 1.0 or 100%). As best seen in FIG. 1D, the size and/or arrangement of the cells 34 may not be uniform throughout the microstructure 30. In this embodiment, the outermost layer of the microstructure is formed by a lattice 32' that differs from the inner lattice 32. While both the inner lattice 32 and the outer lattice 32' may both have cells 34 having the same topology (e.g. tetrahedron, for example), they may differ in terms of size of the cells (and thus size of the pores defined thereby), arrangement of the cells (e.g. periodic or aperiodic) and/or more or less densely packed (e.g. different packing factors P).

In the embodiment depicted in FIGS. 1A-1D, and as best seen in FIG. 1D, the outermost surface/layers of the microstructure 30 within the region 25 of the implant 30 have a lattice 32' defining smaller sized cell 34 and/or a greater density of arrangement of the cells (i.e. in both cases, defining smaller sized pores), relative to the cells of the inner lattice 32 of the microstructure 30. Accordingly, the pore size within the outer lattice 32' of the microstructure 30, which are located on the outwardly facing surfaces of the implant 30 and thus which will come into direct contact with the bone tissue within which the implant 20 is disposed, is smaller than the pore size of the inner lattice 32 of the microstructure.

Some of the cells 34 of a given lattice 32 may be closed on one or more of their sides, to prevent bone ingrowth in certain regions if desired. Accordingly, the cells 34 having one or more closed sides may include a fully closed cell, wherein the cell is still composed of struts forming the selected topology but these struts are enclosed by membranes, for example, such as to form a closed cell. Such closed cells may be included, for example, within a central portion of an implant 20 where bone ingrowth is not required.

The microstructure 30 can be made of a single lattice 32, or as will be further explained below, multiple lattices 32. Each of the multiple lattices 32 can have a given arrangement of cells 34 which has different cell properties than the cells 34 of an adjacent lattice 32.

The microstructure 30 can be a standalone structure which forms part of the implant 20. It thus serves as a biocompatible microstructural framework which provides structural support and defines a bone ingrowth medium. As such, the porous microstructure 30 can be a substitute for cancellous or cancellous and cortical bone tissue, and serve as a cell and tissue reception material. The microstructure 30 of the implant 20 can be made of any suitable biocompatible material, such as stainless steel, cobalt chrome, titanium, aluminum, and alloys thereof. Specifically, in one particular exemplary embodiment, the biocompatible metal used is $Ti_6Al_4V$.

The microstructure 30 can also form a coating applied to the implant 20. Some non-limitative examples of its use as a coating include: a porous coating for vertebral implants, a hip implant, a knee implant, an elbow implant, a shoulder implant, a wrist implant, an ankle implant, a tumor, a trauma, or a dental implant.

Some non-limitative factors which may determine the extent of the region 24 on the external surface 22 include the type of implant and intended location within the body, the local bone tissue against which the implant 20 will be implanted, the health characteristics of the patient, and the ingrowth characteristics of the local bone tissue. It can thus be appreciated that the implant 20 can be adapted to the specific requirements of the anatomic location by, among other things, adjusting the extent of the region 24 of the external surface 22.

For the sole purposes of illustration, the implant 20 is shown in FIG. 1A-1D is a femoral implant as part of a hip replacement system. However, the implants as described herein can be any prosthesis or implantable device which is placed into a patient in proximity to her/his bone tissue in order to facilitate ingrowth of the local bone tissue into the implant 20 or its external surface 22, while reproducing the strength of the local bone tissue. Some non-limitative examples of forms and configurations that the implant 20 may take include the following: an augment to provide an alternative to allografts, a fusion device, a spacer and/or an implant used in spine, hip, knee, ankle, shoulder, elbow, tumor, trauma or dental surgery.

Referring now to FIGS. 2A to 2D, some non-limiting examples of microtruss lattice structures 32 which make up all or a portion of the present microstructure 30 are shown. Each microtruss lattice 32 is composed of a predetermined arrangement of a specific type or types of cells 34, which collectively make up the lattices 32 of the microstructure 30.

Before detailing the specific cell topologies and lattice structures of FIGS. 2A-2D, it is pertinent to first ensure that the terminology used herein to describe the differences between these cells and lattices is clear. In this regard, and as will be seen, microtruss lattice 132, 232, 332, 432 of cells 134, 234, 334, 434 can have a periodic or an aperiodic (i.e. non-periodic) arrangement of the cells, and can have a packing factor (or P value) less than or equal to 1.0 (100%).

The term "periodic" refers to the repeatability of the cells 34 in this arrangement, in that each cell 34 has translational symmetry with adjacent cells 34 throughout the volume of the lattice 32. The term "aperiodic", or non-periodic, refers to the lack of repeatability of the cells 34 in their arrangement, in that each cell 34 has a skewed orientation with respect to an adjacent cell 34 such that the lattice 32 itself does not have overall translational symmetry.

The packing factor (P) is a measure of the "stackability" or tessellation of the cells 34 with respect to one another within their lattice 32. It is determined by calculating the volume of the cell 34 or multiple cells 34, and dividing this value by the volume of a selected portion of the lattice 32 that compromises more cells 34. A packing factor P of 1.0 or 100% therefore indicates that the cells 34 are fully packed tightly together, without any gaps between adjacent cells, wherein each and every strut and edge 36 of each cell 34 is connected to a corresponding strut and edge 36 of a neighbouring cell 34. There are therefore no gaps, or volumetrically insignificant gaps, between the cells 34 in the lattice 32 when the packing factor is 100%. As the packing factor P decreases in value away from 1.0 or 100%, the gaps between adjacent cells 34 increase in volume. This may result from one or more edges 36 of each cell 34 not being connected to an edge 36 of an adjacent cell 34. The orientation of the stacked cells 34 within the lattice 32 can also vary.

Figure 2A:
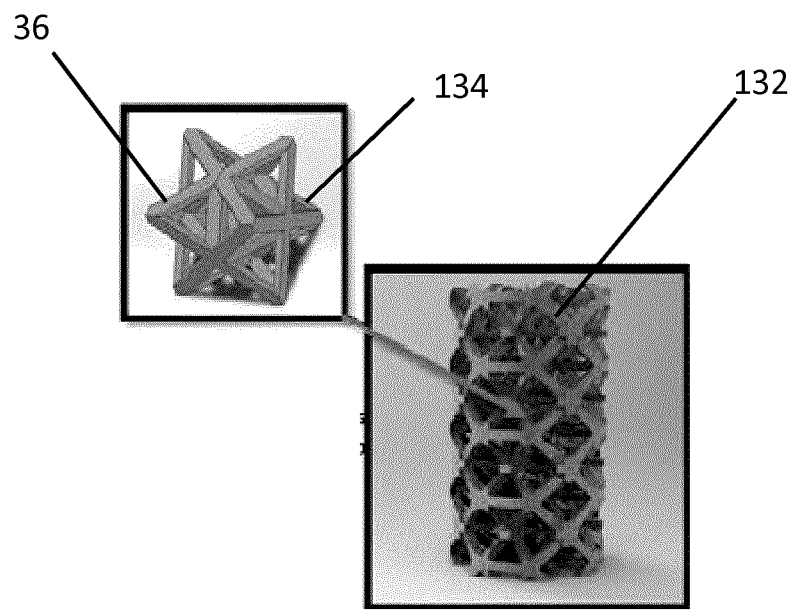
FIG. 2A is a schematic view of a periodic lattice of cells and a corresponding cell of the cell porous microstructure of FIG. 1A, according to another embodiment of the present disclosure.

FIG. 2A shows a lattice 132 composed of cells 134 having an Octet Truss cell topology. The lattice 132 is periodic and has a packing factor P of about 1.0 (100%). It is formed by combining the Octet Truss cells 134 in translational symmetry to substantially fill the space between adjacent cells 134 so that no gaps between cells 134 are formed.

Figure 2B:
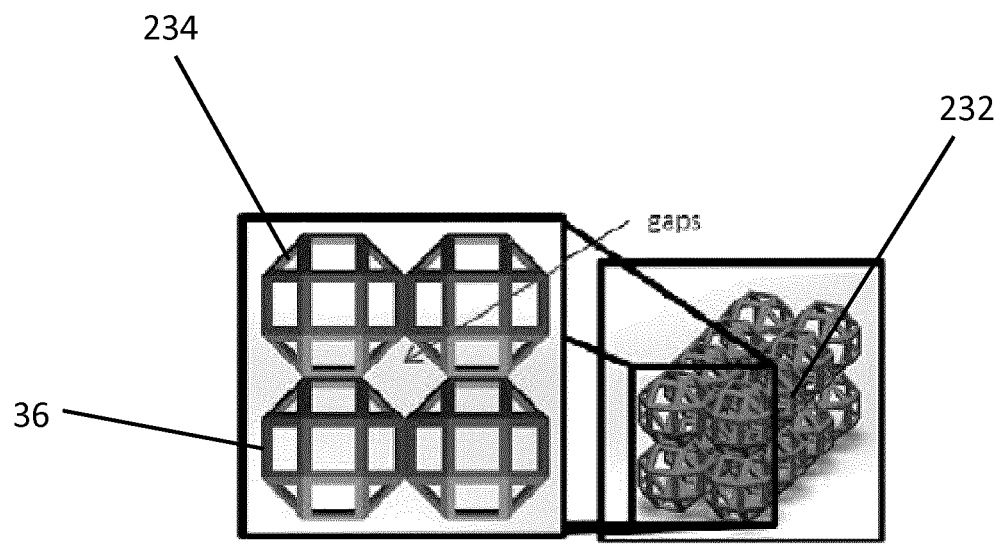
FIG. 2B is a schematic view of another periodic lattice of cells and a corresponding cell of the cell porous microstructure of FIG. 1A, according to yet another embodiment of the present disclosure.

FIG. 2B shows a lattice 232 composed of cells 234 having an Octahedron cell topology. The lattice 232 is periodic and has a packing factor P of less than 1.0. It is formed by patterning the Octahedron cells 234 in a translational manner to form a skewed octahedron arrangement, which creates gaps between adjacent cells 234.

Figure 2C:
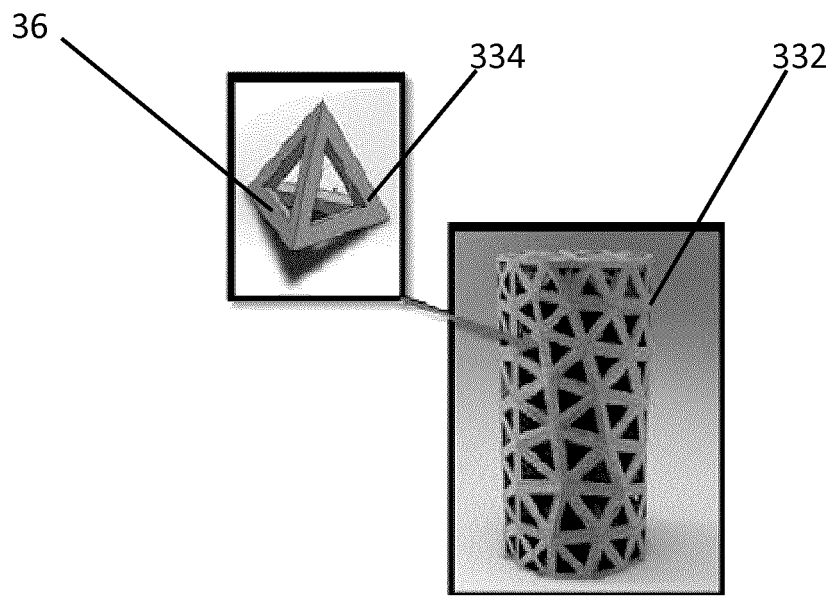
FIG. 2C is a schematic view of an aperiodic lattice of cells and a corresponding cell of the cell porous microstructure of FIG. 1A, according to yet another embodiment of the present disclosure.

FIG. 2C shows a lattice 332 composed of cells 334 having a Tetrahedron cell topology. FIGS. 1A and 1B show a microstructure 30 made of a plurality of such lattices. The lattice 332 is aperiodic and has a packing factor P of about 1.0. It is formed by skewing each Tetrahedron cell 334 relative to an adjacent cell 334 to substantially fill the space between adjacent cells 334 so that no gaps between cells 334 are formed.

Figure 2D:
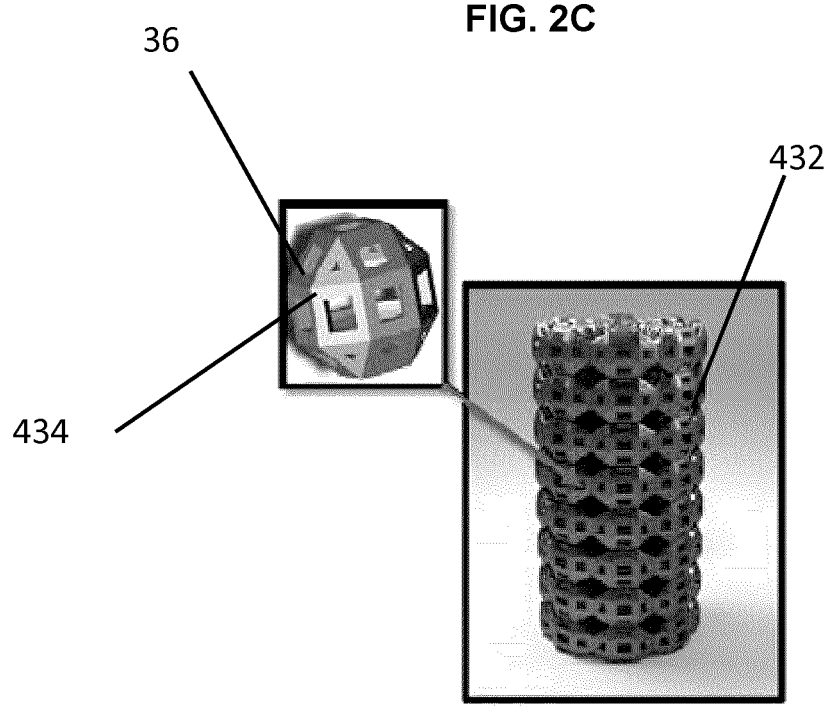
FIG. 2D is a schematic view of another aperiodic lattice of cells and a corresponding cell of the cell porous microstructure of FIG. 1, according to yet another embodiment of the present disclosure.

FIG. 2D shows a lattice 432 composed of cells 434 having an Octahedron cell topology. The lattice 432 is aperiodic and has a packing factor P of less than 1.0. It is formed by skewing each Octahedron cell 434 relative to an adjacent cell 434 and packing them together to form a skewed cell arrangement, such that the space between adjacent cells 434 is not completely filled.

Figure 2E:
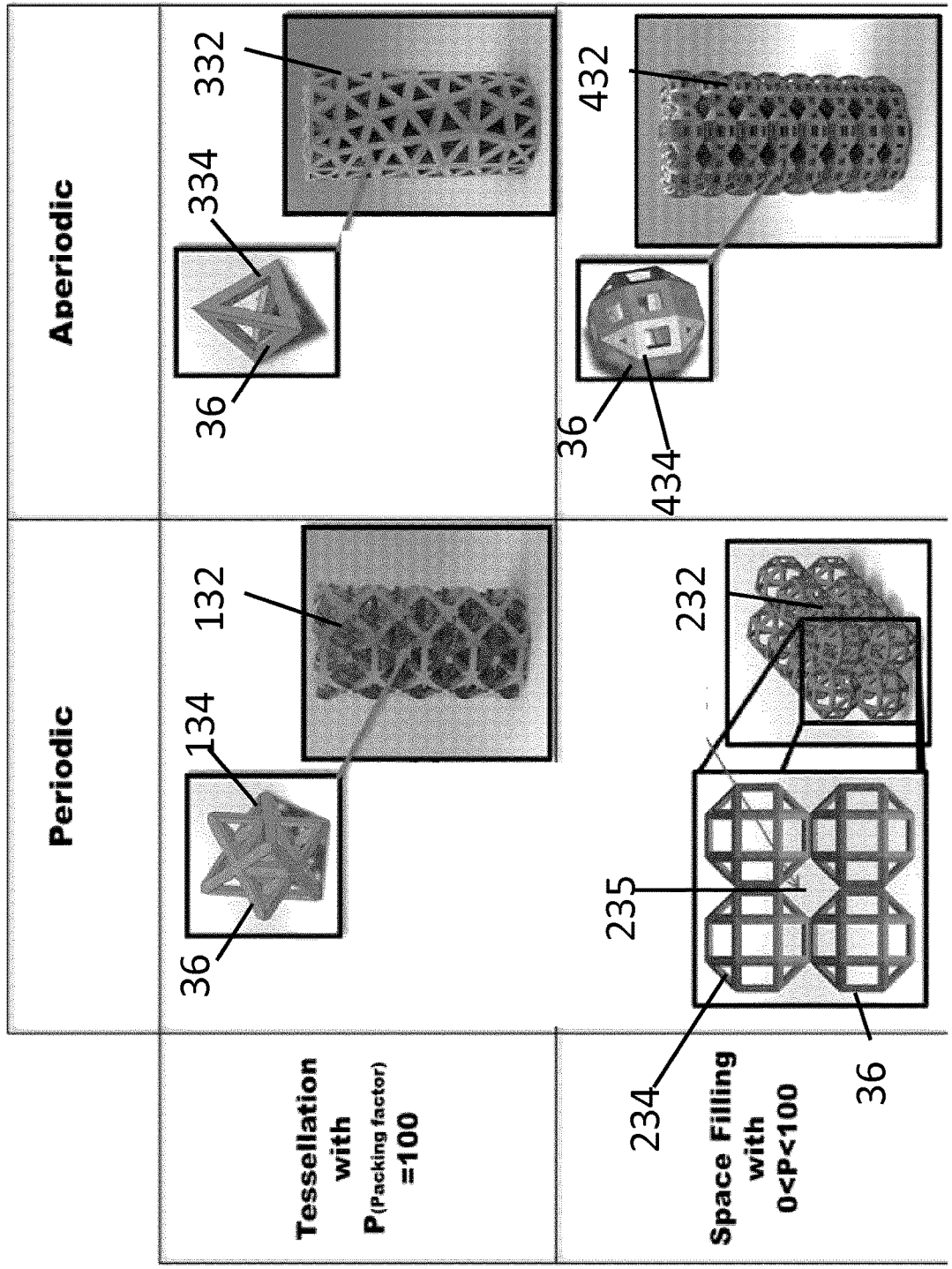
FIG. 2E is a table showing the cell lattices of FIGS. 2A-2D, showing their relative cellular characteristics in terms of periodicity (periodic or aperiodic) and tessellation (packing factor)
Figure 2F:
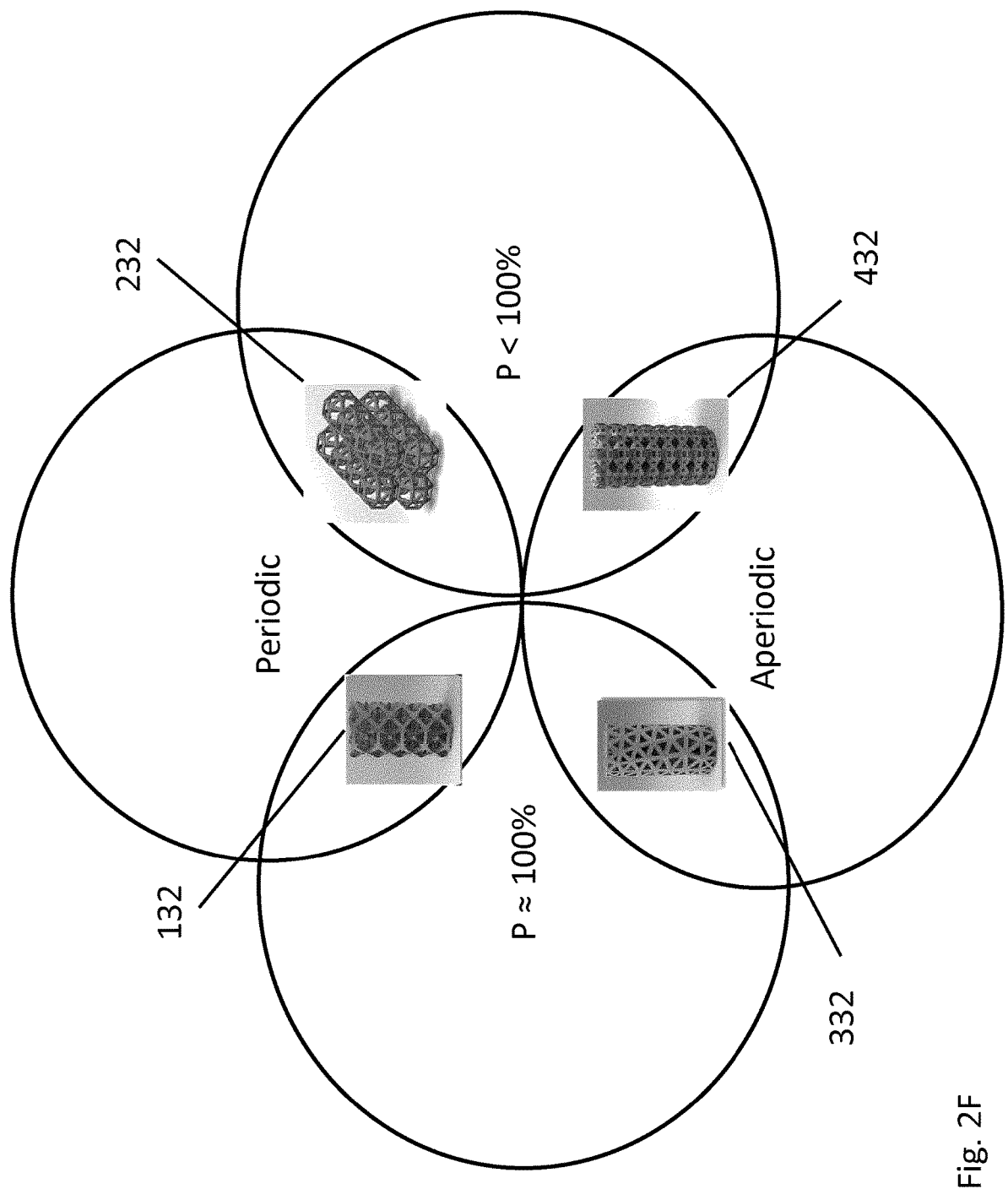
FIG. 2F is a Venn-diagram showing the degree of interconnectivity for the cell lattices of FIGS. 2A-2D.

The inter-relationship between each of the above-described lattices having either period or aperiodic cell arrangements and their respective packing factor P, may be better appreciated from FIGS. 2E and 2F. The table of FIG. 2E shows the cell lattices of FIGS. 2A-2D, classified by their relative cellular characteristics in terms of periodicity (periodic or aperiodic) and tessellation (packing factor).

As can be seen in FIG. 2E, both the octet truss lattice 132 and the octahedron lattice 232 have periodic arrangement of their respective cells 134 and 234. In both of these cases, the lattices have translational symmetry and can be obtained by "copying and pasting", or forming each next cell (i.e. a repeating unit) by laterally translating a previous cell within a plane or space. However, while both the octet truss lattice 132 and the octahedron lattice 232 are periodic, their tessellation differs and thus they have different packing factors. The octet truss lattice 132 is formed with its unit cells 134, each having an octet truss topology, completely filling the volumetric space without any gaps or overlaps. As described above, the octet truss lattice 132 therefore has a packing factor of 1.0 or 100%. The octet truss cells 134 are therefore fully packed tightly together, without any volumetric significant gaps between adjacent cells, wherein each and every strut and edge 36 of each cell 134 is connected to a corresponding strut and edge 36 of a neighbouring cell 134. In contrast, and as seen in FIG. 2E and its counterpart image in FIG. 2B, the octahedron lattice 232 has a packing factor of less than 1.0 or 100%, as the translation of the cells 234 having an octahedron topology creates a lattice 232 with volumetric gaps 235 between the cells 234, even though the cells 234 having adjoining edges 36 that connect with the corresponding strut and edge 36 of the next adjacent cell 234.

Referring still to FIG. 2E, both the tetrahedron lattice 332 and the octahedron lattice 432 have an aperiodic (i.e. non-periodic) arrangement of their unit cells 334 and 434, respectively having a tetrahedron topology and an octahedron topology. Accordingly, the aperiodic tetrahedron lattice 332 and octahedron lattice 432 both have a scaled (or "skewed") repeating unit cell packed within a plane or space. However, the tetrahedron lattice 332 is fully tessellated and thus has a packing factor of 1.0 or 100%. Accordingly, the cells 334 are packed together without any gaps and overlaps formed therebetween. In contrast, when the cells 434 of the octahedron lattice 432 are packed together they do not occupy 100% of the given volumetric space and thus volumetric gaps exist between the adjacent octahedron shaped cells 434. The octahedron lattice 432 therefore has a packing factor of less than 1.0 or 100%, and cells 434 which are aperiodically arranged.

FIG. 2F is a Venn-diagram showing the degree of inter-connectivity for the cell lattices of FIGS. 2A-2D, and their respective tessellation (packing factor) and periodicity (periodic or aperiodic) as shown in FIG. 2E.

It will be appreciated that one or more of these lattices 32 can be combined together to make the microstructure 30. The properties of the lattice 32, 132, 232, 332, 432 and its respective cells can also vary. The lattice can have a porosity of about 30% or more, where porosity is determined by calculating the collective volume of open spaces or voids within the microstructure 30, a lattice, or a section thereof, and dividing it by the dimensional volume of the selected body. Other possible porosity values, in increasing order of preference of the described exemplary embodiments, include between about 40% and 80%, greater than about 50%, greater than about 60% and between 30% and 40%. The porosity of the lattice, and thus microstructure 30, can thus be selected based on the specific application of the implant 20 in order to encourage bone ingrowth and provide the required structural support.

Although closed cells are possible, as described above, a majority of the cells 34, 134, 234, 334, 434, etc., in the lattice of the microstructure 30 are "open" cells, in that in that they permit material (such as, but not limited to, bone tissue) and/or fluids to traverse at least partially, and alternatively completely, through the interior of each cell 34. The lattices forming the present microstructure 30 are preferably formed in majority by such open cells (i.e. greater than 50% of the cells are at least partially open cells). The microstructure 30 may therefore be referred to herein as a porous material, and more specifically may have a given porosity range as described, however it is to be understood that a certain number of cells 34, etc. may be in fact be closed cells, without preventing the entire structure 30 from being defined as porous.

Because the lattice 32 forming the microstructure 30 is "designed", in that its specific structural characteristics or properties (cell topology, porosity, cell wall or strut thickness, pore size, etc.) are pre-selected prior to manufacturing the implant, each cell 34 which forms the lattice 32 necessarily has a predetermined cell topology which can be either constant amongst the cells 34, or which can alternately vary from cell to cell throughout the lattice provided the nodal connectivity among the cells 34 is preserved.

The lattices 32, 132, 232, 332, 432, etc. can therefore be designed to be either homogenous, wherein the properties are substantially uniform or constant throughout, or graded (i.e. heterogeneous), wherein the properties of the lattice 32 (and thus the cells 34 forming same) vary as desired throughout the portion of the implant 20 having the microstructure 30. In the case of graded or heterogeneous lattices, the high-strength porous biomaterial and implants formed thereby as described herein improve upon the inventor's own graded cellular implants for bone replacement as described in WO 2013/091085, the entire content of which is incorporated herein by reference.

The term "predetermined" as used herein refers to the selection of one or more cell topologies, or other cell properties, prior to manufacturing the implant 20 in order to adapt the implant 20 to the specific needs of the patient. This is in contrast with certain conventional implantable bodies whose cell topologies and properties are defined randomly during the manufacture of the implantable body (as is the case for foam-based materials, for example). Each cell 34 also has multiple peripheral edges 36. Each lattice 32 is formed by connecting one or more edges 36 of each cell 34 to corresponding edges 36 of adjacent, neighbouring cells 34. This defines the interconnectivity of the lattice 32, and thus of the microstructure 30 as a whole. It can thus be appreciated that the interconnectivity of cells 34 creates a porous lattice 32 which encourages bone ingrowth therein because of the interconnected network of fluid and material passages through the cells 34.

EXPERIMENTAL EXAMPLE

Figures 3A, 3B:
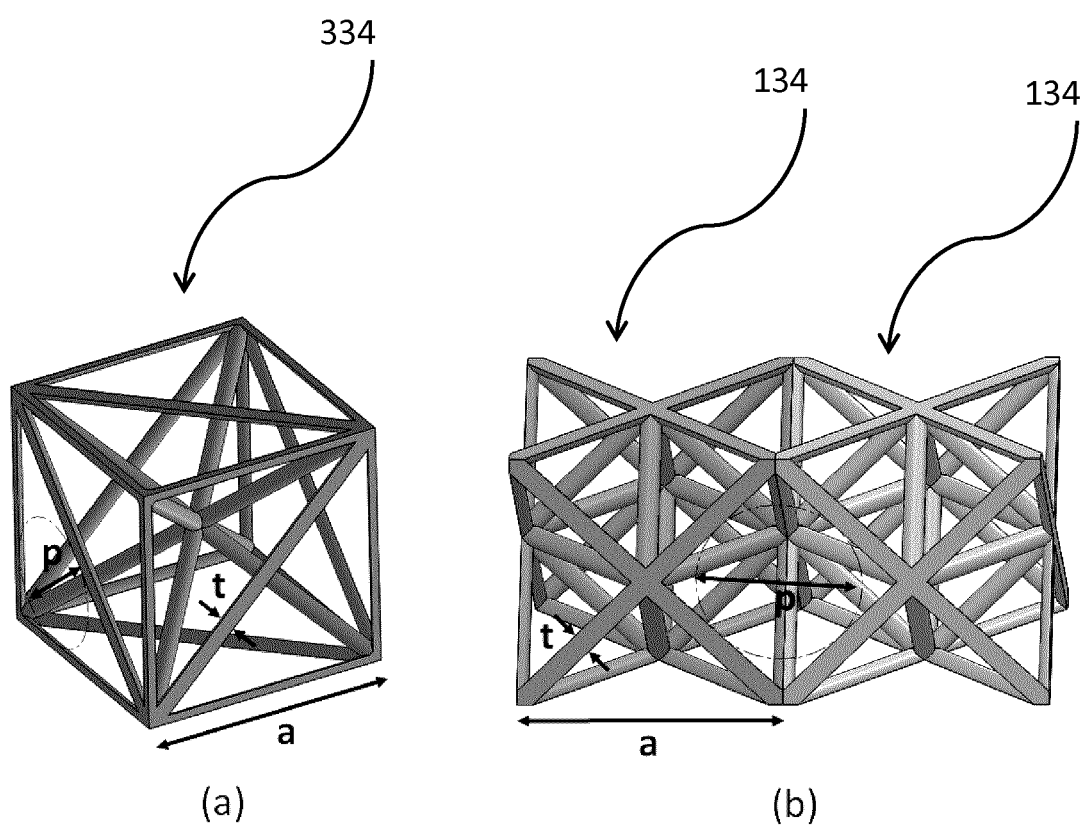
FIG. 3A is a perspective view of a single unit cell of the lattice of FIG. 2C, the cell having a tetrahedron topology.
FIG. 3B is a perspective view of two cells of the lattice of FIG. 2A, each cell having an octet truss topology, the two cells being arranged together without gaps therebetween such as to define a packing factor of 100%.

Referring now to FIGS. 3A and 3B, unit cells forming the fully tessellated lattices 132 and 332 described above, namely the octet truss cell 134 (FIG. 3B) the tetrahedron cell 334 (FIG. 3A) respectively, will now be described in further detail. Both of these cell topologies are high-strength, stretching dominated, topologies which were designed, fabricated and tested by the inventors in the manner described below.

Using Selective Laser Melting (SLM), two design points were fabricated within constraints for both tetrahedron 334 and octet truss 134 cells, in order to assess the bone ingrowth and apposition at four and eight week intervals in a canine model. Bone ingrowth was shown to occur with these two high strength lattice cell topologies. To further investigate the mechanical strength of these two cell topologies, the inventors manufactured eight design points with SLM, and the deviation was quantified between designed and manufactured morphological parameters using Micro CT testing, including quasi-static compression tests to determine the effective elastic modulus in compression and the 2% offset yield of the manufactured samples.

As shown in FIGS. 3A and 3B, a tetrahedron cell 334 and an Octet truss cell 134 were cell topologies selected for the construction and testing of the structural porous biomaterial 30. Both the tetrahedron topology lattice 332 and the octet strut topology lattice 132 are "stretching dominated" lattice structures for all loading states, as they satisfy the known Maxwell's criterion for static determinacy. Based upon the topology of these unit cells, lattice materials can be generally classified into two main groups, namely, bend-dominated and stretch-dominated. The cells of a bending-dominated lattice collapse by local bending of the cell struts at the nodes with lower mechanical properties. In stretching-dominated lattice materials, on the other hand, cells collapse by stretching of its struts, which provide a higher stiffness and strength per unit mass as compared to bend-dominated topologies. For load bearing orthopedic applications, a fully porous biomaterial should have sufficient mechanical strength to withstand a combination of physiological loadings. Selecting a stretching-dominated lattice, such as the tetrahedron topology lattice 332 and the octet strut topology lattice 132, allows the designer to create a structure with sufficient mechanical properties while obtaining higher porosity for bone ingrowth.

To develop a parametric model for each of the unit cells 334 and 134, it was observed that the overall cell geometry is controlled by two parameters, strut thickness 't' and unit cell size 'a', provided the cross-section of all the struts is circular and un-tapered along their length. Using these two design parameters, the unit cell topologies can be scaled to any desired size with resultant porosity and pore size. The pore size 'p' for this study was measured at the bone-implant interface and is defined by the diameter of a largest circle that can be inscribed within a polygon face of a unit cell or a polygon formed by two adjacent unit cells. Porosity is also measured from the percentage of void space in a solid unit cell using the following formula:

$$\text{Porosity (\%)} = \left(1 - \frac{V_p}{V_s}\right) \times 100$$

where Vp is the volume of the porous unit cell and Vs is the volume of the completely solid unit cell. In this parametric model, strut thickness and cell size were systematically varied, and the resultant pore size and porosity were recorded.

Figure 4A:
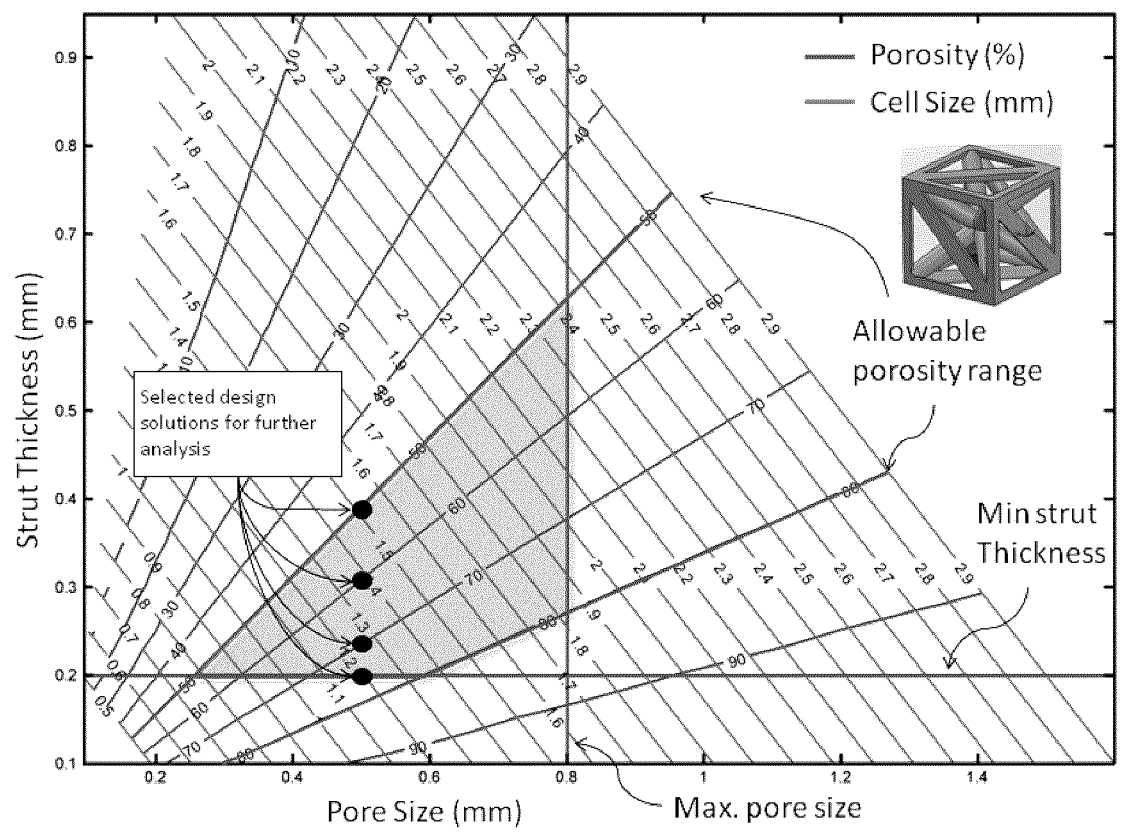
FIG. 4A is a graph showing pore size vs. strut thickness for the cell of FIG. 3A having a tetrahedron topology, with imposed constraints of manufacturing, pore size and porosity range.
Figure 4B:
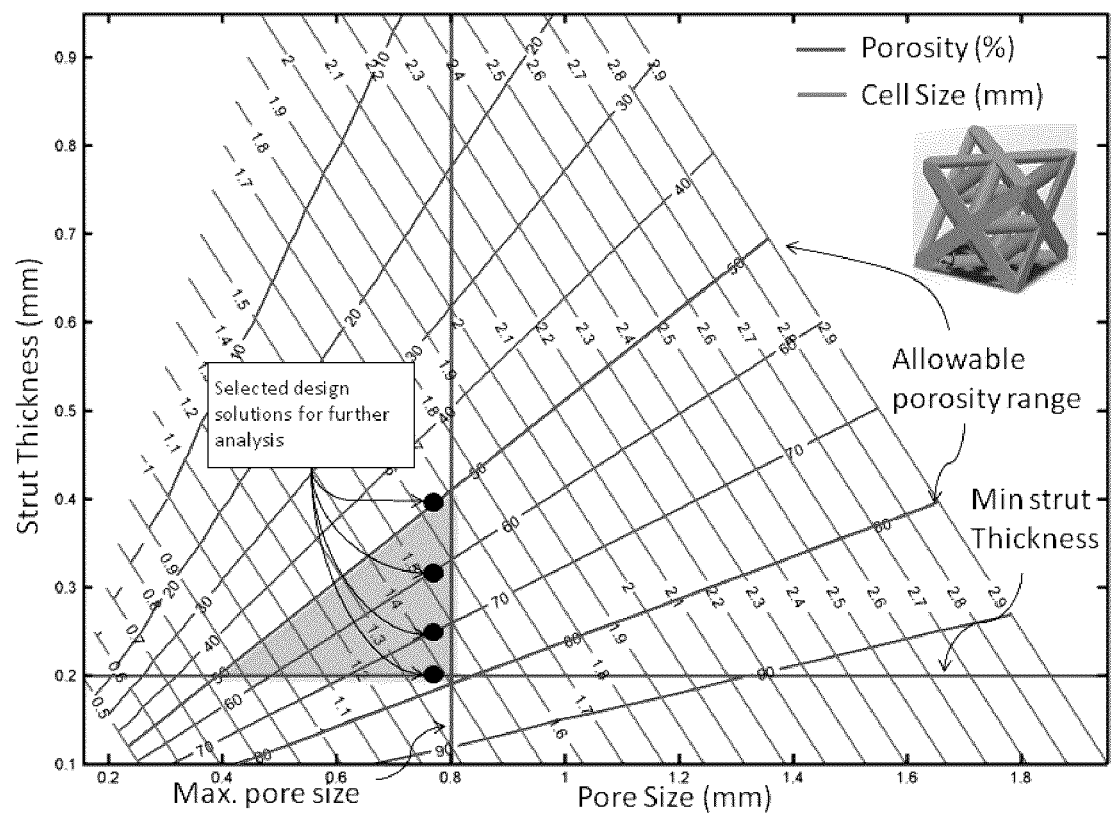
FIG. 4B is a graph showing pore size vs. strut thickness for the cell of FIG. 3B having an octet truss topology, with imposed constraints of manufacturing, pore size and porosity range.

The results of this are plotted in FIGS. 4A and 4B as contour plots, with strut size on the y axis and pore size on the x axis. Values of porosity and cell size are also plotted as isometric lines, as shown in FIGS. 4A-4B. Moving along constant porosity and cell size lines clearly shows how pore size and wall thickness changes. This chart, therefore, provide a clear understanding of how the morphological parameter of a unit cell are interconnected. However, to find the feasible design space for a unit cell topology to be used as structural porous biomaterial, it is important to identify and add constraints to the design charts. The following are two major types of constraints which are important to consider:
1. Bone ingrowth requirements: for bone ingrowth, pore size and porosity of the lattice should be within a suitable range. It has been shown that the optimal porosity and the pore size range for bone ingrowth requirements is considered to higher than 50% and 50 microns to 800 microns, respectively. These form an upper and lower bound for the porosity and pore size which are added to the design chart with lines as shown in FIG. 4A-4B.
2. Manufacturing constraints: for the cellular material manufacturing the current AM technologies have one main limitation. Most of the current technologies such as SLM and EBM are limited to produce a conservative wall thickness (strut thickness) of 200 microns although this limit is process-dependent and can be lower.

Referring now to FIGS. 4A-4B, design parameters were established in order to establish a feasible range of properties of the design cells. As can been seen in the graphs of FIGS. 4A-4B, a minimum strut thickness and a maximum pore size were selected, as was an allowable porosity range. As can be seen in FIGS. 4A-4B, a minimum strut thickness of 0.2 mm was selected and the maximum pore size was 0.8 mm. While the strut thickness of 0.2 mm (200 um) was selected largely based on current manufacturing limitations, it is to be understood that a strut thickness of less than 200 um may also be possible. For example, struts in the range of 170-200 um may already be possible, and therefore it is envisioned than smaller strut thicknesses will be possible as additive manufacturing advancements develop. In this example, the allowable porosity range selected was between 50% and 80%. However, a porosity of as little as 30% and as much as 90% may also be used. These parameters accordingly provide for a range of feasible design solutions for each of these cell topologies, as graphically depicted within the shaded region of these graphs. A solution space of the feasible designs was thus found, and within this solution zone are acceptable design solutions based on the defined criteria. Different unit cell topologies result in different solution spaces. The solution space for the octet truss unit cell (FIG. 4B) is smaller when compared to the solution space of the tetrahedron based unit cell (FIG. 4A). As depicted in these design charts, at a given cell size and a strut thickness the octet truss unit cell is denser than the tetrahedron based topology. Additionally, the size of the pores at the octet truss surface is also larger than the tetrahedron based topology, so based on the imposed constraints, the solution space is limited.

To understand how morphological parameters of the unit cells govern the mechanobiological properties of structural porous biomaterials, a number of representative points were selected within these solution spaces for each of the topologies, and then manufactured to perform mechanical and biological testing. The deviation of morphological parameters of the porous structures from the designed values after manufacturing was also quantified. The selection of representative points, the manufacturing process, and mechanobiological testing are discussed in the following sections.

To experimentally validate the feasibility of the solution space of the design charts, representative samples were selected and manufactured with selective laser melting (SLM). The morphological properties of these samples, including pore size, porosity, wall thickness and cell size, are measured and compared with nominal design values. The samples are also mechanically tested under uniaxial compression test, and the effective uniaxial Young's modulus and yield strength are measured. The following criteria are used to select the representative design solutions for mechanical evaluation purposes:

Four representative design solutions for each topology are chosen at 50%, 60%, 70% and 75% porosity values. This range of porosity covers the entire porosity range for the feasible design solution space. The porosity of the octet truss and tetrahedron where kept as close as possible to these nominal values while respecting the aforementioned constraints. The pore size is kept constant throughout the relative density range within each topology that corresponds to the pore size used in the bone ingrowth study.

The strut thickness is kept constant across topologies for each value of relative density. This limits the variability that may arise from manufacturing deviations (e.g. variation in the manufactured strut thickness) that may arise due to the AM process limitations.

Considering these requirements, four representative design solutions were chosen for tetrahedron and octet truss lattice, as depicted in FIGS. 4A and 4B respectively. For each selected design, five replicates were prepared according to the ISO 13314:2011 guidelines for the mechanical testing of porous and cellular materials. Table 1 below lists the parameter values for selected solutions for each topology. The identified solutions closely match the desired values of the porosities, and the strut thicknesses of both topologies at the corresponding porosity are identical. Additionally, for each unit cell type a constant pore size (i.e. 500 micron for the tetrahedron based unit cell and 770 microns for the octet truss unit cell) was imposed. The geometric details of the test specimens for the mechanical strength analysis are also provided in Table 1 below. The specimens had a prismatic geometry, and their spatial dimensions i.e. (height, width and depth) are at least 10 times the average pore size, as per the ISO 13314:2011 standard. Moreover, the specimen length to edge length ratio is between 1 and 2.

TABLE 1

Details of the test samples prepared for further analysis

| Unit cell | # | Porosity | Strut Thickness (mm) | Unit Cell Size (mm) | Pore Size (mm) | Height (mm) | Width (mm) | Depth (mm) |
|---|---|---|---|---|---|---|---|---|
| Tetrahedron | 1 | 49.8% | 0.39 | 1.52 | 0.5 | 20.15 | 12.55 | 12.55 |
| | 2 | 59.16% | 0.31 | 1.385 | 0.5 | 18.31 | 11.39 | 11.39 |
| | 3 | 68.85% | 0.24 | 1.27 | 0.5 | 16.75 | 10.4 | 10.4 |
| | 4 | 74.74% | 0.2 | 1.2 | 0.5 | 15.8 | 9.8 | 9.8 |
| Octet truss | 1 | 50.03% | 0.4 | 1.66 | 0.77 | 21.98 | 13.68 | 13.68 |
| | 2 | 59.8% | 0.32 | 1.54 | 0.77 | 20.34 | 12.64 | 12.64 |
| | 3 | 69.7% | 0.25 | 1.44 | 0.77 | 18.97 | 11.77 | 11.77 |
| | 4 | 77.28% | 0.2 | 1.37 | 0.77 | 18.01 | 11.16 | 11.16 |

To perform biological testing, transcortical implants were designed and manufactured to perform a pilot canine study to measure the amount of bone ingrowth into the porous structure in a period of 4 and 8 weeks. Three tetrahedron and octet truss transcortical implants with a cylindrical shape and an outer diameter of 5 mm and a height of 10 mm were manufactured using the SLM process. The manufactured tetrahedron topology had an average porosity of 61% and pore size of 438 microns. The manufactured octet truss had an average porosity of 76% and pore size of 772 microns. The values of porosity and pore size fall within our defined admissible design region based on bone ingrowth constraints.

For the bone ingrowth portion of the study, two stretching dominated topologies were first selected, namely: octet truss; and tetrahedron based topologies. The primary objective was to determine if bone in growth occurred within the stretching dominated structures. The tetrahedron based transcortical sample has a pore size and porosity of 438 and 55%, respectively, representing a point in the middle of the design space. On the other hand, the selected point for octet truss is close to the upper bound of pore size in the feasible design space with pore size and porosity of 772 and 76%, respectively.

The results of the study to measure the amount of bone ingrowth into the porous structure of these implants over a period of 4 and 8 weeks are shown in FIGS. 5A-5B. As can be seen from FIGS. 5A and 5B, the microstructure composed of a lattice having a tetrahedron based cell topology demonstrated measurable bone ingrowth at both 4 and 8 weeks.

Bone ingrowth into the all transcortical implants after 4 and 8 weeks was accordingly found. The bone ingrowth of the stretching dominated topologies was compared with some of currently used porous coatings, and Trabecular Metal™ tantalum foam.

4 and 6 week canine studies have shown that the amount of bone ingrowth into porous coating varies between about 15% to 50%, while for Trabecular Metal™, the amount of ingrowth is higher and increases from 13% in 2 week to 53% in 4 weeks. As can be seen in Table 2 below, the amount of bone ingrowth for tetrahedron and octet truss samples of the present disclosure is in the range of other porous coating and is lower than Trabecular Metal™. Studies have shown that the amount of bone ingrowth is linearly proportional to porosity of sample. This might be one of possible reasons that the amount of bone ingrowth is lower in our samples compared to Trabecular Metal™ which has porosity of 75 to 85% which is significantly higher than the porosity of manufactured transcortical implants as described above.

One of the main advantageous of manufactured tetrahedral and Octet truss samples compared to Trabecular Metal™ is their mechanical strength.

TABLE 2

Bone ingrowth and measured section porosity for 4 and 8 week intervals.

| Time Period | Femoral Location | Topology | Porosity % | Bone Ingrowth % |
|---|---|---|---|---|
| 4 weeks | Proximal | Tetrahedron | 55.51% | 19.9% |
| | | Tetrahedron | 55.51% | 14.3% |
| | Distal | Octet | 69.88% | 33.6% |
| 8 weeks | Proximal | Octet | 69.88% | 52.9% |
| | | Tetrahedron | 55.51% | 35.3% |
| | Distal | Tetrahedron | 55.51% | 38.9% |

As can be seen in FIG. 5C, the strength of manufactured samples of the fully porous structural biomaterial of the present disclosure is significantly higher than that of Trabecular Metal™. As shown in FIG. 5C, the measured strength (more specifically, yield strength) of the tested samples of fully porous structural biomaterials as described herein is shown for each of four different porosities. Each of these strengths relate to a structural porous biomaterial having a lattice formed by cells having a tetrahedron topology. More particularly, samples of the present porous biomaterial having 50%, 60%, 70% and 75% porosity provided material strengths of 195.08 MPa, 118.31 MPa, 107.63 MPa and 64.49 MPa, respectively. As such, the present porous biomaterial can be said to provided a yield strength of greater than 190 MPa at 50% porosity, greater than 115 MPa at 60% porosity, greater than 100 MPa at 70% porosity and greater than 60 MPa at 75% porosity. In comparison, market available porous biomaterials, such as the tantalum foam of Trabecular Metal™, has a strength of 34.7-40.8 MPa for 50%-60% porosity.

Furthermore, because the samples of the presently described materials are manufactured with additive manufacturing, the porosity gradient can be tightly controlled in order minimize stress shielding while maintaining sufficient strength. High strength porous structures can be manufactured where its interface layer with bone has optimal pore size and porosity for bone ingrowth, while internal microstructure is designed with lower porosity to have high mechanical strength to support physiological loading.

Other Cell Topologies

Although several main cell topologies have been described above, different cell topologies can also be used and the topology of the cells within each lattice or combination of lattices can also vary. The topology can be any one, or a combination, of the solids known as "Johnson Solids". More specifically, examples of the cell topology that fall within this group include: an octet truss, a tetrahedron, an octahedron, a body-centered cube (BCC), a face-centered cube (FCC), a rhombicuboctahedron, a rhombic dodecahedron, or any combination of one or more of these typologies (e.g. an FCC-BCC). The possible cell topologies disclosed herein are not limited to this list, and also include any other cell topology that provides the requisite interconnectivity for a given application, and meets the desired criteria for strength and bone ingrowth. The number of cell topologies and their combinations which are possible with the implant 20 disclosed herein is in contrast with some conventional implantable bodies which use cells having only one or two cell topologies. Such a limited number of cell topologies in conventional implantable bodies can limit the "stackability" or tessellation of its cells 34.

The pore size of the cells 34 can also vary. The pore size is a measure of the passage defined by each cell 34, and helps to facilitate bone ingrowth, particularly on the external surface 22 of the implant 20. For example, certain bone tissue will not engage in bone ingrowth with the neighbouring implant 20 if its cells 34 have too large or too small a pore size. Therefore, the mean pore size of the cells 34 can be between about 50 µm and about 800 µm. The pore size can vary throughout the implant 20 in order to optimize bone ingrowth on the external surface 22 and maintain structural strength throughout the rest of the implant 20.

The strut thickness, or thickness of the walls of each of the cells 34, can also vary. The wall thickness of each cell 34 helps to determine the structural support that its lattice 32, and ultimately, the microstructure 30, can provide. For example, thicker cell walls may provide greater structural support while thinner cell walls may provide less structural support. The wall thickness can also be selected as a function of the bone ingrowth requirements for the implant 20. As such, and in order to allow the implant 20 to be designed to suit the needs of a specific patient, the cell wall thickness of each cell 34 can be between about 70 µm and about 400 µm. Other values for the cell wall thickness are also possible and can be selected based on at least the following criteria: prevalent manufacturing capabilities concerning the ability to manufacture relatively thin cell walls, the strength required for the implant 20 at the local bone tissue, and the desired and designed arrangement of cells 34. The strut thickness, or thickness of the walls of each of the cells 34 can vary throughout the implant 20 in order to optimize bone ingrowth on the external surface 22 and maintain structural strength throughout the rest of the implant 20.

In one embodiment of the present implant, the above described properties (i.e. porosity, cell topology, cell pore size, and cell wall strut thickness) are constant (i.e. homogeneous) for all the cells 34 forming the lattice 32. Alternately, the lattice structure may be formed of a single cell topology throughout a majority of the implant, except for at one or more external surfaces which has a different cell topology. The cell topology selected for the cells on the external surface(s) of the implant may, for example, be better suited for osseointegration and/or fibrous attachment, whereas the cell topology internally within the implant may be selected more for its strength properties. Alternatively still, in another embodiment the implant 20 can have a "graded" distribution of cell properties in its external surface 22 or region 24, such that the properties of each cell 34 may vary from cell to cell, between sections of a single lattice 32, and/or between several different lattices 32 themselves. For example, the microstructure 30 on the proximal region of the femoral implant 20 of FIG. 1 can have one or more lattices 32 with a low porosity and having cells 34 with greater strut thicknesses, such as to reinforce this particular region of the implant 20. The microstructure 30 on the distal intramedullary stem region of the same implant 20 can have one or more lattices 32 having greater porosities and lower cell strut thicknesses. Alternately still, any one portion of the implant may have a graded distribution of cell properties, such as to better replicate the structural properties of cancellous bone, for example. It will be appreciated that other combinations of properties, for other types of implants 20, are possible and also within the scope of the present disclosure.

Certain additional alternatives and features may also be incorporated into the cells and/lattice of the porous microstructure 30, in order to further improve their mechanical properties including, but not limited to, yield strength, stiffness and fatigue resistance.

For example, the intersection and joints where the struts of each unit cell meet each other can be designed and locally reinforced with an arc, fillet, chamfer, or by adding extra material to improve its mechanical properties in terms of yield strength, stiffness, and fatigue resistance. Accordingly, any of the above-described cells 34, 134, 234, 334, 434, etc., can include filets formed at the junction of each strut with its adjoining strut, either within a single unit cell or between interconnected struts of adjoining cells. These fillets can also have continuity in curvature in order to minimize stress concentration at the joints between struts and thus to improve fatigue resistance of the entire cell of the lattice.

Additionally, the cross section of each individual strut of the unit cells can be designed and modified to improve the mechanical properties of the resulting unit cell. The cross section shape and area of each strut can therefore be made to vary throughout a length of the strut, throughout the cell and/or throughout the entire microstructure of the implant. The unit cell cross section shape and size can therefore be designed to produce directional and anisotropic behavior to the unit cell structure to improve its mechanical properties in certain directions. The cross-sectional shape and size can also vary throughout the implant to provide reinforcement at certain locations inside the implant structure, and thereby improving the mechanical properties of the implant. The changes of the cross section shape and size throughout the implant can also follow a predefined or an optimized pattern or a function.

Further still, the surface of each of the struts forming the open unit cells can be designed to have "waviness" and/or other surface roughness, in order to better tailor the stiffness of the unit cell to match the stiffness of bone. In one embodiment, for example, the surface roughness can be designed in the range of 10 µm to 500 µm.

Referring now to FIGS. 6-16, having described some of the properties of the various lattices and cells above, examples of possible microstructures 30 with specific cell combinations and properties will now be described. These figures contain graphs plotting, on the vertical axis, minimum cell strut thickness versus cell mean pore size, on the horizontal axis, for a given cell topology. Contours representing microstructure 30 and/or lattice porosities are imposed to define the design space for a given cell topology. The darker regions represent a first region of design or manufacturing constraints for the microstructure 30, and the lighter regions represent another region of design or manufacturing constraints.

FIG. 6 shows the design characteristics for a microstructure 30 in accordance with an embodiment characterised by an FCC cell topology, a porosity between about 40% and about 80%, a strut thickness of at least about 200 μm, and a mean pore size between about 50 μm and about 600 μm.

FIG. 7 shows the design characteristics for a microstructure 30 in accordance with an embodiment characterised by a BCC cell topology, a porosity between about 40% and about 60%, a strut thickness of at least about 200 μm, and a mean pore size between about 400 μm and about 600 μm.

FIG. 8 shows the design characteristics for a microstructure 30 in accordance with an embodiment characterised by an FCC-BCC composite cell topology, a porosity between about 40% and about 80%, a strut thickness of at least about 200 μm, and a mean pore size between about 50 μm and about 600 μm.

Figure 9:
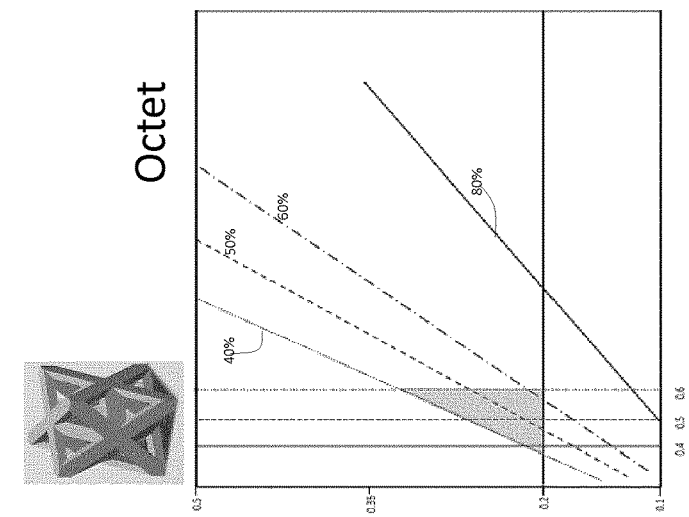
FIG. 9 is a graph showing nominal cell wall thicknesses at different cell mean pore sizes and microstructure porosities for an cell porous microstructure having an Octet Truss cell topology.

FIG. 9 shows the design characteristics for a microstructure 30 in accordance with an embodiment characterised by an Octet Truss cell topology, a porosity between about 40% and about 60%, a strut thickness of at least about 200 μm, and a mean pore size between about 400 μm and about 600 μm.

Figure 10:
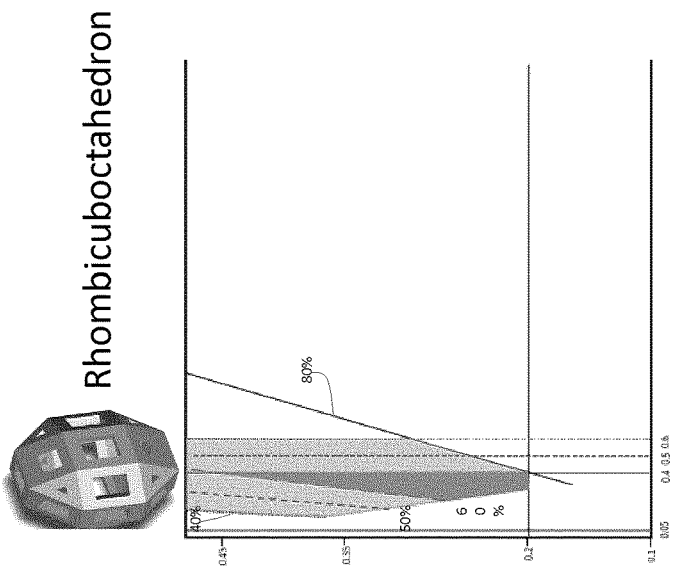
FIG. 10 is a graph showing nominal cell wall thicknesses at different cell mean pore sizes and microstructure porosities for an cell porous microstructure having a Rhombicuboctahedron cell topology.

FIG. 10 shows the design characteristics for a microstructure 30 in accordance with an embodiment characterised by Rhombicuboctahedron cell topology, a porosity between about 40% and about 80%, a strut thickness of at least about 200 μm, and a mean pore size between about 50 μm and about 600 μm.

Figure 11:
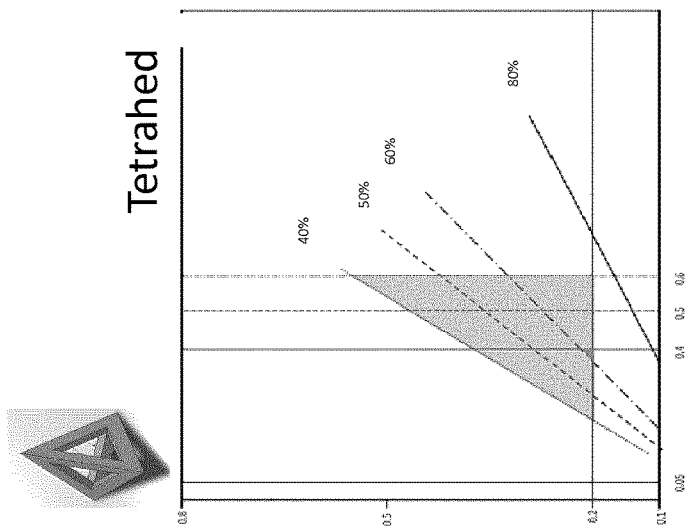
FIG. 11 is a graph showing nominal cell wall thicknesses at different cell mean pore sizes and microstructure porosities for an cell porous microstructure having a Tetrahedron cell topology.

FIG. 11 shows the design characteristics for a microstructure 30 in accordance with an embodiment characterised by a Tetrahedron cell topology, a porosity between about 40% and about 80%, a strut thickness of at least about 200 μm, and a mean pore size between about 50 μm and about 600 μm.

Figures 12, 13, 14:
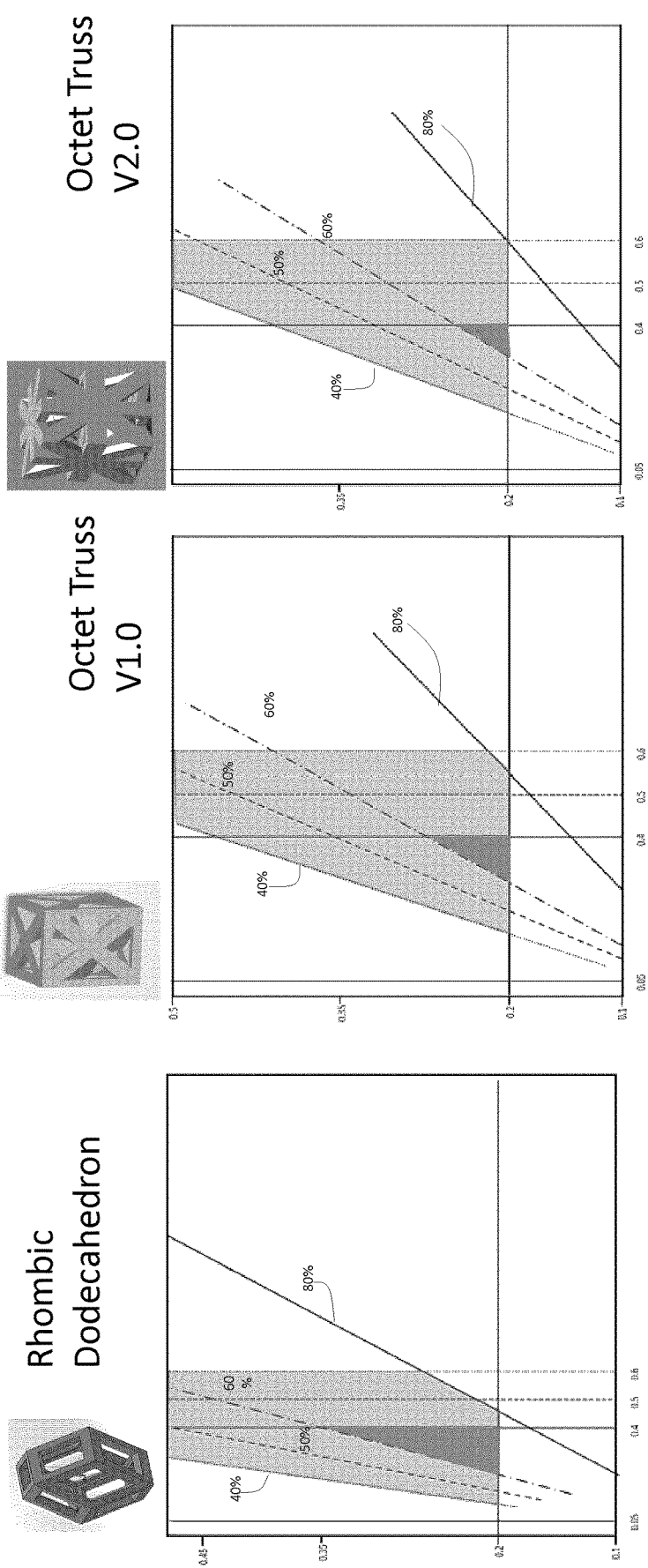
FIG. 12 is a graph showing nominal cell wall thicknesses at different cell mean pore sizes and microstructure porosities for an cell porous microstructure having a Rhombic Dodecahedron cell topology.
FIG. 13 is a graph showing nominal cell wall thicknesses at different cell mean pore sizes and microstructure porosities for an cell porous microstructure having another Octet Truss cell topology.
FIG. 14 is a graph showing nominal cell wall thicknesses at different cell mean pore sizes and microstructure porosities for an cell porous microstructure having yet another Octet Truss cell topology.

FIG. 12 shows the design characteristics for a microstructure 30 in accordance with an embodiment characterised by a Rhombic Dodecahedron cell topology, a porosity between about 40% and about 80%, a strut thickness of at least about 200 μm, and a mean pore size between about 50 μm and about 600 μm.

FIG. 13 shows the design characteristics for a microstructure 30 in accordance with an embodiment characterised by another Octet Truss cell topology, a porosity between about 40% and about 80%, a strut thickness of at least about 200 μm, and a mean pore size between about 50 μm and about 600 μm.

FIG. 14 shows the design characteristics for a microstructure 30 in accordance with an embodiment characterised by yet another Octet Truss cell topology, a porosity between about 40% and about 80%, a strut thickness of at least about 200 μm, and a mean pore size between about 50 μm and about 600 μm.

FIG. 15 shows the design characteristics for a microstructure 30 in accordance with an embodiment characterised by yet another Octet Truss cell topology, a porosity between about 40% and about 80%, a strut thickness of at least about 200 μm, and a mean pore size between about 50 μm and about 600 μm.

FIG. 16 shows the design characteristics for a microstructure 30 in accordance with an embodiment characterised by yet another Octet Truss cell topology, a porosity between about 40% and about 80%, a strut thickness of at least about 200 μm, and a mean pore size between about 50 μm and about 600 μm. Although various designs, forms, and geometries of the Octet Truss topology are shown in FIGS. 9, 13, 14, 15, and 16, it will be appreciated that other geometries for the Octet Truss are possible and within the scope of the present disclosure.

Manufacturing

The implant having the porous microstructure as described herein may be preferably manufacturing using additive manufacturing technologies.

Recent advances in Additive Manufacturing (AM), such as Electron-Beam Melting (EBM), Selective Laser Melting (SLM), Stereolithography Apparatus (SLA), and other additive processes, enable a complex three dimensional structure to be precisely manufactured with controlled architecture. These AM methods enable scaffolds to be reproduced with controlled topology, porosity, pore shape and size, interconnectivity, and mechanical properties, all of which greatly influence osseointegration of the scaffold. Such manufacturing processes are also capable of building porous structures with pore size and porosity gradients. The present porous biomaterial with an optimum microstructure can therefore be designed and manufactured to achieve a desirable mechanical response and functional environment for bone ingrowth.

In the Example above, the cells tested were manufactured as follows. The samples were produced using the SLM process by the Renishaw AM250. The AM250 uses an Nd:YAG laser in Q-switched mode with a maximum power of 200 W and a laser spot diameter of 70 μm. Ti6VAl4 powder (grade II according to ASTM F67, SLM Solutions) is used. The powder size is between 20-70 μm, and 95% of particles have a powder size smaller than 50 μm. The laser parameters were adjusted to an energy density Ev of 63 J/mm$^3$ and a scanning velocity of 260 mm/s. The powder layer thickness was 30 μm. After fabrication, the samples were cleaned from adhering powder particles by compressed air.

More particularly, the presently disclosed method for manufacturing the implant 20 comprises pre-selecting a designed porous lattice microstructure composed of at least some cells. The cells have properties which are predetermined and pre-designed, and therefore the method includes selecting one or more predetermined cell topologies and selecting a predetermined porosity, cell strut thickness and packing factor of the lattice. The implant is then formed using additive manufacturing, which includes forming the designed porous lattice microstructure in at least a region of at least an external surface of the implant adapted to be disposed proximate bone tissue. This ensures that the designed porous lattice microstructure accordingly has the predetermined and selected cell topologies and the predetermined porosity, cell strut thickness and packing factor, and that the arrangement and properties of the cells and properties can be controlled throughout the implant.

Such a non-chemical process of manufacturing the implant 20 provides a measure of predictability, in that it is possible to produce a pre-determined and known distribution of cells and cell properties in the implant 20. This is in contrast to some prior art devices, in which the implant is formed by etching, dissolving, or otherwise chemically removing material from within a chemically-produced metallic foam substrate. It will be appreciated that such techniques do not allow for a high degree of control of the arrangement of the cells, their topology, or their "stackability", in contrast with the disclosed methods and techniques which allow for a highly-customizable implant 20 to be manufactured.

It can be further appreciated that the design (an a-priori determination), and additive manufacturing of the implant 20 allows for the creation of specific and repeatable morphologies for the pores of the cells. These cells, individually and collectively, form microstructure geometries. The lattice can thus be a-priori defined and manufactured with a greater accuracy than that obtainable with chemical-based processes, such as those used to create metallic foams.

According to another aspect, there is provided a method for manufacturing a porous microstructure along a region of an external surface of an implant. The method includes repeatedly depositing layers of material on the region to form at least one lattice of cells, each cell having a predetermined cell topology and a plurality of edges. One or more edges of each cell connect to an adjacent cell along a corresponding edge thereof, and the cells collectively have a periodic arrangement or an aperiodic arrangement within the lattice.

The method can be performed by a suitable additive manufacturing machine, such as those using techniques such as, but not limited to, electron beam melting and selective laser sintering.

In light of the preceding, the porous microstructure 30 disclosed herein has load bearing capacity, and can have lattice and cell properties that mimic those of natural cancellous and/or cortical bone. The microstructure 30 is made of biocompatible metal materials, and with its anatomic location-specific properties it encourages bone tissue ingrowth while providing structural support. The cellular microstructure 30 can also be tailored to provide mechanical biocompatibility so as to create mechanical properties that match locally those of the surrounding bone.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure, and such modifications are intended to fall within the appended claims.

The invention claimed is:

1. An implant one or more surfaces of which are adapted to be disposed against bone tissue, the implant comprising:
   an external surface at least a portion of which is comprised of a porous microstructure and adapted to abut the bone tissue, the porous microstructure formed by an additive-manufactured lattice of a plurality of cells, the cells having a predetermined cell topology that is designed and pre-selected prior to manufacturing such as to have predetermined structural characteristics, the predetermined cell topology being selected from a group consisting of: octet truss; tetrahedron; octahedron; Body-Centered Cube (BCC); Face-Centered Cube (FCC); rhombicuboctahedron; rhombic dodecahedron; and any combination of one or more of these cell topologies;
   wherein each of the cells having said predetermined cell topology is formed by a plurality of struts defining pores of the cell therebetween, at least one strut of each cell connecting to a strut of an adjacent one of the cells within the lattice along a corresponding edge thereof, and wherein regardless of the predetermined cell topology selected from said group, the struts having a strut thickness of between 70 μm and 400 μm, the pores of the cell having a mean pore size of between 50 μm and 800 μm;
   wherein the lattice defines a predetermined and designed tessellation and arrangement of said cells forming the lattice, the lattice having a porosity of between 30% and 99%.

2. The implant of claim 1, wherein said tessellation and said arrangement of the cells are uniform throughout the lattice.

3. The implant of claim 1, wherein the arrangement of the cells within the lattice is fully periodic or fully aperiodic.

4. The implant of claim 1, wherein the arrangement of the cells within the lattice is a combination of periodic and aperiodic.

5. The implant of claim 1, wherein the cells are fully tessellated and a packing factor of the cells connected to one another within the lattice is about 100%.

6. The implant of claim 1, wherein gaps are defined between adjacent and interconnected cells within the lattice, a packing factor of the cells being less than 100%.

7. The implant of claim 1, wherein the cells of the lattice comprise two or more different cell topologies.

8. The implant of claim 1, wherein the porous microstructure is made from a biocompatible material selected from the group consisting of: Titanium; Steel; CoCr; Tantalum; and alloys of each thereof.

9. The implant of claim 1, wherein the porosity of the lattice is between 40% and 80%.

10. The implant of claim 1, wherein the mean pore size of each of said cell varies in said porous microstructure.

11. The implant of claim 1, wherein at least one of a cross-sectional shape and a cross-sectional area of the struts of the cells vary within said porous microstructure.

12. The implant of claim 1, wherein the cell topology of said cell includes a Face-Centered Cube (FCC) and modifications thereof, the lattice has a porosity between 30% and 80%, a strut thickness of each said cell is at least about 70 μm, and a mean pore size of each said cell is between 50 μm and 800 μm.

13. The implant of claim 1, wherein the cell topology of each said cell includes a Body-Centered Cube (BCC) and modifications thereof, the porous microstructure has a porosity between 30% and 80%, a strut thickness of each said cell is at least about 70 μm, and a mean pore size of each said cell is between 50 μm and 800 μm.

14. The implant of claim 1, wherein the cell topology of each said cell includes a composite of Face-Centered Cube (FCC) and Body-Centered Cube (BCC), the lattice has a porosity between 30% and 80%, a strut thickness of each said cell is at least about 70 μm, and a mean pore size of each said cell is a maximum of about 800 μm.

15. The implant of claim 1, wherein the cell topology of each said cell includes an octet truss, the porous microstructure has a porosity between 30% and 80%, a strut thickness of each said cell is at least about 70 μm, and a mean pore size of each said cell is a maximum of about 800 μm.

16. The implant of claim 1, wherein the cell topology of each said cell includes a rhombicuboctahedron and modifications thereof, the lattice has a porosity between 30% and 80%, a strut thickness of each cell is at least about 70 μm, and a mean pore size of each said cell is a maximum of about 800 μm.

17. The implant of claim 1, wherein the cell topology of each said cell includes a rhombic dodecahedron and modifications thereof, the lattice has a porosity between 30% and 80%, a strut thickness of each said cell is at least about 70 μm, and a mean pore size of each said cell is a maximum of about 800 μm.

18. The implant of claim 1, wherein the struts of the cells have a surface roughness thereon, the surface roughness being in the range of 10 μm to 500 μm.

19. The implant of claim 1, wherein one or more joints between said struts of the cells have local reinforcement to improve the mechanical properties of the cells formed thereby, without materially affecting the pore size.

20. The implant of claim 19, wherein the local reinforcement includes at least one of an arc, fillet, chamfer or added material.

21. The implant of claim 1, wherein the cell topology is one of a tetrahedron and an octet truss.

22. The implant of claim 1, wherein the porous microstructure has a strength of greater than 190 MPa at 50% porosity, greater than 115 MPa at 60% porosity, greater than 100 MPa at 70% porosity and greater than 60 MPa at 75% porosity.

23. A structural porous biomaterial comprising a designed microtruss having a porous lattice microstructure composed of cells, a majority of the cells being open and having tissue reception surfaces permitting bone ingrowth therein, said cells having a predetermined cell topology that is designed and pre-selected prior to manufacturing such as to have predetermined structural characteristics, the predetermined cell topology selected from the group consisting of: octet truss; tetrahedron; octahedron; Body-Centered Cube (BCC); Face-Centered Cube (FCC); rhombicuboctahedron; rhombic dodecahedron; and any combination of one or more of these cell topologies; and wherein the cells of the porous lattice microstructure are arranged to form an interconnected network of said cells, the porous lattice microstructure having a porosity of between 30% and 99%, and wherein regardless of the predetermined cell topology selected from said group, each of the cells having said predetermined cell topology have has a mean pore size of between 50 µm and 800 µm and is formed by struts having a cell strut thickness of between 70 µm and 400 µm.

24. The structural porous biomaterial of claim 23, wherein the structural porous biomaterial forms a cancellous or cancellous-cortical bone substitute.

25. The structural porous biomaterial of claim 23, wherein the porous lattice microstructure defines a predetermined and designed tessellation and arrangement of said cells forming the lattice.

26. The implant of claim 1, wherein the porous microstructure is made of $Ti_6Al_4V$.

* * * * *